(12) United States Patent
Haller et al.

(10) Patent No.: US 7,341,729 B2
(45) Date of Patent: *Mar. 11, 2008

(54) RECOMBINANT PARAINFLUENZA VIRUS EXPRESSION SYSTEMS AND VACCINES

(75) Inventors: Aurelia Haller, Boulder, CO (US); Kathleen L. Coelingh, San Francisco, CA (US)

(73) Assignee: MedImmune Vaccines, Inc., Mountain View, CA (US)

( * ) Notice: Subject to any disclaimer, the term of this patent is extended or adjusted under 35 U.S.C. 154(b) by 393 days.

This patent is subject to a terminal disclaimer.

(21) Appl. No.: 10/934,864

(22) Filed: Sep. 3, 2004

(65) Prior Publication Data

US 2005/0147623 A1 Jul. 7, 2005

Related U.S. Application Data

(63) Continuation of application No. 10/252,134, filed on Sep. 20, 2002, now Pat. No. 6,811,784, which is a continuation of application No. PCT/US01/09091, filed on Mar. 21, 2001, which is a continuation of application No. 09/531,375, filed on Mar. 21, 2000, now Pat. No. 6,764,685.

(51) Int. Cl.
*A61K 39/00* (2006.01)

(52) U.S. Cl. ............................ 424/192.1; 424/211.1; 435/69.1

(58) Field of Classification Search ............ 424/192.1, 424/211.1, 204.1; 435/69.1, 6, 345
See application file for complete search history.

(56) References Cited

U.S. PATENT DOCUMENTS

| 5,869,036 | A | 2/1999 | Belshe et al. | |
|---|---|---|---|---|
| 6,764,685 | B1 * | 7/2004 | Haller et al. | 424/211.1 |
| 6,811,784 | B2 * | 11/2004 | Haller et al. | 424/192.1 |

FOREIGN PATENT DOCUMENTS

| WO | WO 89/10405 | | 11/1989 |
|---|---|---|---|
| WO | WO 93/14207 | | 7/1993 |
| WO | WO 97/34008 | | 9/1997 |
| WO | WO 98/53078 | | 11/1998 |
| WO | WO 01/04320 | A1 | 1/2001 |

OTHER PUBLICATIONS

Breker-Klassen et al., 1996, "Comparisons of the F and HN gene sequences of different strains of bovine parainfluenza virus type 3: relationship to phenotype and pathogenicity," Can. J. Vet. Res. 60:228-236.

Dimock and Collins, 1993, "Rescue of synthetic analogs of genomic RNA and replicative-intermediate RNA of human parainfluenza virus type 3," J. Virol. 67:2772-2778.

Durbin et al., 1997, "Recovery of infectious parainfluenza virus type 3 from cDNA," Virol. 235:323-332.

Haller, et al., (2000) "Expression of the Surface Glycoproteins of Human Parainfluenza Virus Type 3 by Bovine Parainfluenza Virus Type 3, a Novel Attenuated Virus Vaccine Vector,"J. Virology 74(24):11626-11635.

Karron et al., 1996, "Evaluation of a live attenuated bovine parainfluenza type 3 vaccine in two- to six-month-old infants," Pediatr. Infect. Dis. J. 15:650-654.

Karron et al., 1995, "A Live Attenuated Bovine Parainfluenza Virus Type 3 Vaccine is Safe, Infectious, Immunogenic, and Phenotypically Stable in Infants and Children," J. of Infect. Diseases 171:1107-1114.

Klippmark et al., 1990, "Antigenic variation of human and bovine parainfluenza virus type 3 strains," J. Gen. Virol. 71:1577-1580.

Palese et al., 1996, "Negative-strand RNA viruses: genetic engineering and applications," Proc. Natl. Acad. Sci. USA 93:11354-11358.

Schmidt et al., 2000, "Bovine parainfluenza virus type 3 (BPIV3) fusion and hemagglutinin-neuraminidase glycoproteins make an important contribution to the restricted replication of BPIV3 in primates,"J. Virol. 74(19):8922-8929.

Shibuta et al., 1979, "Characterization of bovine parainfluenza virus type 3", Microbiol. Immunol. 23:617-628.

Skiadopoulos et al., 2001, "A chimeric human-bovine parainfluenza virus type 3 expressing measles virus hemagglutinin is attenuated for replication but is still immunogenic in rhesus monkeys," J. Virol. 75(21):10498-10504.

Skiadopoulos et al., 1998, "Three amino acid substitutions in the L protein of the human parainfluenza virus type 3 cp45 live attentuated vaccine candidate cnontribute to its temperature-sensitive and attenuation phenotypes," J. Virol. 72(3):1762-1768.

Tao et al., 1999, "A live attenuated chimeric recombinant parainfluenza virus (PIV) encoding the internal proteins of PIV type 3 and the surface glycoproteins of PIV type 1 induces complete resistance to PIV1 challenge and partial resistance to PIV3 challenge," Vaccine 17:1100-1108.

Tao et al., 1998, "Recovery of a fully viable chimeric human parainfluenza virus (PIV) type 3 in which the hemagglutinin-neuraminidase and fusion glycoproteins have been replaced by those of PIV type 1," J. Virol. 72:2955-2961.

* cited by examiner

*Primary Examiner*—Ali R. Salimi

(57) ABSTRACT

The present invention relates to recombinant bovine para influenza virus (bPIV) cDNA or RNA which may be used to express heterologous gene products in appropriate host cell systems and/or to rescue negative strand RNA recombinant viruses that express, package, and/or present the heterologous gene product. The chimeric viruses and expression products may advantageously be used in vaccine formulations including vaccines against a broad range of pathogens and antigens.

21 Claims, 2 Drawing Sheets

1 2 3 4 5 6 7   8 9 10 11

RECOMBINANT PARAINFLUENZA VIRUS EXPRESSION SYSTEMS AND VACCINES

Figure 1:
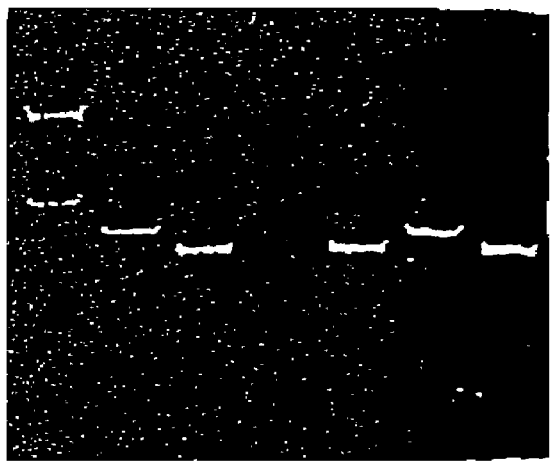
Figure 1:
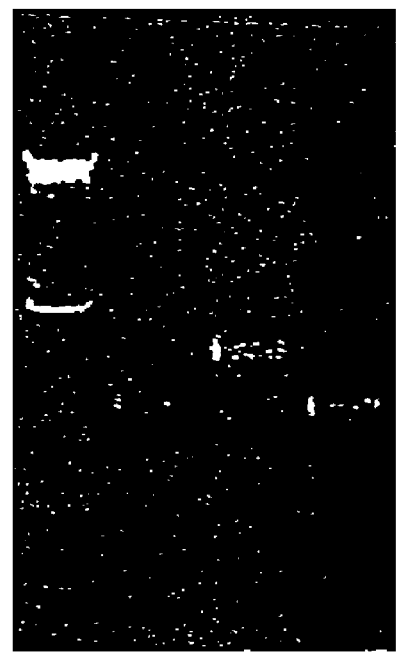

This application is a continuation of U.S. application Ser. No. 10/252,134 filed Sep. 20, 2002, issued as U.S. Pat. No. 6,811,784 on Nov. 2, 2004, which is a continuation of application No. PCT/US01/09091 filed on Mar. 21, 2001, which is a CON of U.S. non-provisional patent application Ser. No. 09/531,375, filed Mar. 21, 2000, now U.S. Pat. No. 6,764,685 all of which are incorporated herein by reference in their entireties.

1. INTRODUCTION

The present invention relates to recombinant para influenza virus (PIV) cDNA or RNA which may be used to express heterologous gene products in appropriate host cell systems and/or to rescue negative strand RNA recombinant viruses that express, package, and/or present the heterologous gene product. The chimeric viruses and expression products may advantageously be used in vaccine formulations including vaccines against a broad range of pathogens and antigens. The present invention relates to chimeric viruses comprising human PIV or bovine PIV genomic sequences and nucleotide sequences encoding heterologous antigens. In particular, the present invention encompasses vaccine preparations comprising chimeric PIV expressing antigenic glycoproteins of another species of PIV or of another virus. In one embodiment, the present invention relates to a cross-species bPIV3/hPIV3 that is viable and infectious.

The present invention also relates to genetically engineered para influenza viruses that contain modifications and/or mutations that make the recombinant virus suitable for use in vaccine formulations, such as an attenuated phenotype or enhanced immunogenicity. The present invention relates to the use of the recombinant para influenza viruses and viral vectors against a broad range of pathogens and/or antigens, including tumor specific antigens. The invention is demonstrated by way of examples in which recombinant para influenza virus cDNA or RNA was constructed containing heterologous gene coding sequences in the positive or negative polarity which were then used to rescue the negative strand RNA chimeric virus particles and/or to express the heterologous gene products which may then be utilized in vaccine preparations. In particular, such heterologous gene sequences include sequences derived from another species of PIV.

2. BACKGROUND OF THE INVENTION

Parainfluenza viral infection results in serious respiratory tract disease in infants and children. (Tao, et al., 1999, Vaccine 17: 1100-08). Infectious para influenza viral infections account for approximately 20% of all hospitalizations of pediatric patients suffering from respiratory tract infections worldwide. Id. A vaccine has not yet been approved for the prevention of PIV related disease, nor is there an effective antiviral therapy once disease occurs.

PIV is a member of the *paramyxovirus* genus of the paramyxovirus family. PIV is made up of two structural modules: (1) an internal ribonucleoprotein core, or nucleocapsid, containing the viral genome, and (2) an outer, roughly spherical lipoprotein envelope. Its genome is a single strand of negative sense RNA, approximately 15,456 nucleotides in length, encoding at least eight polypeptides. These proteins include the nucleocapsid structural protein (NP, NC, or N depending on the genera), the phosphoprotein (P), the matrix protein (M), the fusion glycoprotein (F), the hemagglutinin-neuraminidase glycoprotein (HN), the large polymerase protein (L), and the C and D proteins of unknown function. Id.

The para influenza nucleocapsid protein (NP, NC, or N) consists of two domains within each protein unit including an amino-terminal domain, comprising about two-thirds of the molecule, which interacts directly with the RNA, and a carboxyl-terminal domain, which lies on the surface of the assembled nucleocapsid. A hinge is thought to exist at the junction of these two domains thereby imparting some flexibility to this protein (see Fields et al. (ed.), 1991, *Fundamental Virology Second Edition*. Raven Press, New York, incorporated by reference herein in its entirety). The matrix protein (M), is apparently involved with viral assembly and interacts with both the viral membrane as well as the nucleocapsid proteins. The phosphoprotein (P), which is subject to phosphorylation, is thought to play a regulatory role in transcription, and may also be involved in methylation, phosphorylation and polyadenylation. The fusion glycoprotein (F) interacts with the viral membrane and is first produced as an inactive precursor, then cleaved post-translationally to produce two disulfide linked polypeptides. The active F protein is also involved in penetration of the para influenza virion into host cells by facilitating fusion of the viral envelope with the host cell plasma membrane. Id. The glycoprotein, hemagglutinin-neuraminidase (HN), protrudes from the envelope allowing the virus to contain both hemagglutinin and neuraminidase activities. HN is strongly hydrophobic at its amino terminal which functions to anchor the HN protein into the lipid bilayer. Id. Finally, the large polymerase protein (L) plays an important role in both transcription and replication. Id.

In one embodiment, the present invention relates to the construction of a cross-species bovine PIV3/human PIV3 chimeric virus vaccine. Bovine parainfluenza virus was first isolated in 1959 from calves showing signs of shipping fever. It has since been isolated from normal cattle, aborted fetuses, and cattle exhibiting signs of respiratory disease (Breker-Klassen, et al., 1996, Can. J. Vet. Res. 60: 228-236). See also Shibuta, 1977, Microbiol. Immunol. 23 (7), 617-628. Human and bovine PIV3 share neutralizing epitopes but show distinct antigenic properties. Significant differences exist between the human and bovine viral strains in the HN protein. In fact, while a bovine strain induces some neutralizing antibodies to hPIV infection, a human strain seems to induce a wider spectrum of neutralizing antibodies against human PIV3 (Klippmark, et al., 1990, J. Gen. Vir. 71: 1577-1580). Thus, it is expected that the bPIV3/hPIV3 chimeric virus vaccine of the present invention will also induce a wider spectrum of neutralizing antibodies against hPIV3 infection while remaining attenuated and safe for human use. Other chimeric parainfluenza virus vaccines are also contemplated by the invention.

The replication of all negative-strand RNA viruses, including PIV, is complicated by the absence of cellular machinery required to replicate RNA. Additionally, the negative-strand genome can not be translated directly into protein, but must first be transcribed into a positive-strand (mRNA) copy. Therefore, upon entry into a host cell, the genomic RNA alone cannot synthesize the required RNA-dependent RNA polymerase. The L, P and N proteins must enter the cell along with the genome on infection.

It is hypothesized that most or all of the viral proteins that transcribe PIV mRNA also carry out their replication. The mechanism that regulates the alternative uses (i.e., transcription or replication) of the same complement of proteins has not been clearly identified but appears to involve the abundance of free forms of one or more of the nucleocapsid proteins. Directly following penetration of the virus, transcription is initiated by the L protein using the negative-sense RNA in the nucleocapsid as a template. Viral RNA synthesis is regulated such that it produces monocistronic mRNAs during transcription.

Following transcription, virus genome replication is the second essential event in infection by negative-strand RNA viruses. As with other negative-strand RNA viruses, virus genome replication in PIV is mediated by virus-specified proteins. The first products of replicative RNA synthesis are complementary copies (i.e., plus-polarity) of PIV genome RNA (cRNA). These plus-stranded copies (anti-genomes) differ from the plus-strand mRNA transcripts in the structure of their termini. Unlike the mRNA transcripts, the anti-genomic cRNAs are not capped and methylated at the 5' termini, and are not truncated and polyadenylated at the 3' termini. The cRNAs are coterminal with their negative strand templates and contain all the genetic information in the complementary form. The cRNAs serve as templates for the synthesis of PIV negative-strand viral genomes (vRNAs).

Both the bPIV negative strand genomes (vRNAs) and antigenomes (cRNAs) are encapsidated by nucleocapsid proteins; the only unencapsidated RNA species are virus mRNAs. For bPIV, the cytoplasm is the site of virus RNA replication, just as it is the site for transcription. Assembly of the viral components appears to take place at the host cell plasma membrane and mature virus is released by budding.

2.1. Engineering Negative Strand RNA Viruses

The RNA-directed RNA polymerases of animal viruses have been extensively studied with regard to many aspects of protein structure and reaction conditions. However, the elements of the template RNA which promote optimal expression by the polymerase could only be studied by inference using existing viral RNA sequences. This promoter analysis is of interest since it is unknown how a viral polymerase recognizes specific viral RNAs from among the many host-encoded RNAs found in an infected cell.

Animal viruses containing plus-sense genome RNA can be replicated when plasmid-derived RNA is introduced into cells by transfection (for example, Racaniello et at., 1981, Science 214:916-919; Levis, et al., 1986, Cell 44: 137-145). In the case of poliovirus, the purified polymerase will replicate a genome RNA in in vitro reactions and when this plus-sense RNA preparation is transfected into cells it is infectious (Kaplan, et al., 1985; Proc. Natl. Acad. Sci. USA 82:8424-8428). However, the template elements which serve as transcription promoter for the poliovirus-encoded polymerase are unknown since even RNA homopolymers can be copied (Ward, et al., 1988, J. Virol. 62: 558-562). SP6 transcripts have also been used to produce model defective interfering (DI) RNAs for the Sindbis viral genome. When the RNA is introduced into infected cells, it is replicated and packaged. The RNA sequences which were responsible for both recognition by the Sindbis viral polymerase and packaging of the genome into virus particles were shown to be within 162 nucleotides (nt) of the 5' terminus and 19 nt of the 3' terminus of the genome (Levis, et al., 1986, Cell 44: 137-145). In the case of brome mosaic virus (BMV), a positive strand RNA plant virus, SP6 transcripts have been used to identify the promoter as a 134 nt tRNA-like 3' terminus (Dreher, and Hall, 1988, J. Mol. Biol. 201: 31-40). Polymerase recognition and synthesis were shown to be dependent on both sequence and secondary structural features (Dreher, et al., 1984, Nature311: 171-175).

The negative-sense RNA viruses have been refractory to study with respect to the sequence requirements of the replicase. The purfied polymerase of vesicular stomatitis virus is only active in transcription when virus-derived ribonucleoprotein complexes (RNPs) are included as template (De and Banerjee, 1985, Biochem. Biophys. Res. Commun. 126: 40-49; Emerson and Yu, 1975, J. Virol. 15: 1348-1356; Naito and Ishihama, 1976, J. Biol. Chem. 251: 4307-4314). With regard to influenza viruses, it was reported that naked RNA purified from virus was used to reconstitute RNPs. The viral nucleocapsid and polymerase proteins were gel-purified and renatured on the viral RNA using thioredoxin (Szewczyk, et al., 1988, Proc. Natl. Acad. Sci. USA, 85: 7907-7911). However, these authors did not show that the activity of the preparation was specific for influenza viral RNA, nor did they analyze the signals which promote transcription.

It is now possible to recover negative strand RNA viruses using a recombinant reverse genetics approach. See U.S. Pat. No. 5,166,057 to Palese et al., incorporated herein by reference in its entirety. Although this method was originally applied to engineer influenza viral genomes (Luytjes et al. 1989, Cell 59: 1107-1113; Enami et al. 1990, Proc. Natl. Acad. Sci. USA 92: 11563-11567), it has been successfully applied to a wide variety of segmented and nonsegmented negative strand RNA viruses, including rabies (Schnell et al. 1994, EMBO J. 13:4195-4203); respiratory syncytial virus (Collins et al. 1991, Proc. Natl. Acad. Sci. USA 88:9663-9667); and Sendai virus (Park et al. 1991, Proc. Natl. Acad. Sci. USA 88:5537-5541; Kato et al., 1996, Genes Cells 1: 569-579).

The reverse genetics has been successfully applied to rescue other minigenomes of PIV3, i.e., cDNAs that encode vRNA in which all the viral genes were replaced by a negative-sense copy of the CAT gene (Dimock et al., 1993, J. Virol. 67: 2772-2778). In this study, reverse genetics was employed to identify the minimum PIV3 3' terminal and 5' terminal nucleotide sequences required for replication, gene expression and transmission of PIV. An infectious human PIV3 was rescued when the reverse genetics approach was successfully applied to recover virus from cells transfected with cDNAs, separately encoding a complete hPIV3 genome, hPIV3 nucleocapsid protein N, the phosphoprotein P and polymerase protein L (Durbin & Banerjee, 1997, J. Virol. 235:323-332).

The reverse genetics approach has also been applied to engineer recombinant parainfluenza genomes for the production of recombinant human PIV for the purpose of generating vaccines. See WO 98/53078, entitled "Production of Attenuated Parainfluenza Virus Vaccines From Cloned Nucleotide Sequences," by Murphy et al. However, the approach has never been heretofore applied to successfully engineer a PIV3 containing heterologous sequences which has suitable properties for use in vaccines to be administered to humans.

3. SUMMARY OF THE INVENTION

Recombinant parainfluenza virus cDNA and RNA is described which may be used with expression plasmids and/or helper virus to express heterologous gene products in appropriate host cells and/or to rescue the heterologous gene in virus particles. In one embodiment, the present invention relates to engineering recombinant bovine or human parainfluenza viruses which express heterologous antigens. In particular, the invention relates to engineering a recombinant Kansas-strain bovine parainfluenza type 3 virus containing heterologous sequences as well as cDNA and RNA molecules coding for the same. The present invention also relates to recombinant PIV which contain modifications which result in phenotypes which make the chimeric virus more suitable for use in vaccine formulations, and which contain heterologous genes, including genes of other species of PIV, other viruses, pathogens, cellular genes, tumor antigens, etc.

The present invention relates to vaccines comprising the chimeric viruses and vectors described herein. The present invention also relates to vaccine formulations suitable for administration to humans, as well as veterinary uses. For example, the vaccines of the present invention may be designed for administration to humans, including children, domestic animals, including cats and dogs; wild animals, including foxes and racoons; livestock and fowl, including horses, cattle, sheep, turkeys and chickens.

In another embodiment, the present invention relates to engineering recombinant parainfluenza viruses and viral vectors which encode combinations of genes from different strains of PIV or which contain heterologous genes including genes of other viruses, pathogens, cellular genes, tumor antigens, etc. Thus, the invention encompasses recombinant parainfluenza vectors and viruses which are engineered to encode genes from different species and strains of the parainfluenza virus, including the F and HN genes of human PIV3.

In a further embodiment, rescue of the chimeric virus or expression products may be achieved by reverse genetics in host cell systems where the host cells are transfected with chimeric cDNA or RNA constructs. The RNA templates of the present are prepared by transcription of appropriate DNA sequences with a DNA-directed RNA polymerase. The resulting RNA templates are of the negative-polarity and contain appropriate terminal sequences which enable the viral RNA-synthesizing apparatus to recognize the template. Alternatively, positive-polarity RNA templates which contain appropriate terminal sequences which enable the viral RNA-synthesizing apparatus to recognize the template, may also be used. Expression from positive polarity RNA templates may be achieved by transfection of plasmids having promoters which are recognized by the DNA-dependent RNA polymerase. For example, plasmid DNA encoding positive RNA templates under the control of a T7 promoter can be used in combination with the vaccinia virus T7 system.

Bicistronic mRNAs can be constructed to permit internal initiation of translation of viral sequences and allow for the expression of foreign protein coding sequences from the regular terminal initiation site, or vice versa. Alternatively, a foreign protein may be expressed from internal transcriptional unit in which the transcriptional unit has an initiation site and polyadenylation site. In another embodiment, the foreign gene is inserted into a PIV gene such that the resulting expressed protein is a fusion protein.

The recombinant mutant parainfluenza viral cDNA and RNA templates of the present invention may be used to transfect transformed cell lines that express the RNA dependent RNA-polymerase and allow for complementation. Alternatively, a plasmid expressing from an appropriate promoter, can be used for virus specific (chimeric) RNA transfection. Complementation may also be achieved with the use of a helper virus which provides the RNA dependent RNA-polymerase. Additionally, a non-virus dependent replication system for parainfluenza virus is also described. The minimum subset of parainfluenza virus proteins needed for specific replication and expression of the virus are the three proteins, L, P, and N or NP, which can be expressed from plasmids by a vaccinia virus T7 or other system. When plasmids encoding an antigenomic copy of the PIV genome are used to supply the viral genome, the minimum subset of virus proteins that may be needed for specific replication and expression of the virus are the L and P proteins, since when the antigenomic copy of the genome is transcribed, the N or NP polymerase protein is the first protein transcribed, thus it is not necessary to additionally provide the N or NP polymerase in trans.

The expression products and/or chimeric virions obtained may advantageously be utilized in vaccine formulations. The expression products and chimeric virions of the present invention may be engineered to create vaccines against a broad range of pathogens, including viral and bacterial antigens, tumor antigens, allergen antigens, and auto antigens involved in autoimmune disorders. In particular, the chimeric virions of the present invention may be engineered to create anti-human parainfluenza vaccines, wherein the bovine parainfluenza fusion (F) and hemagglutinin (HN) glycoproteins are replaced by the human F and HN glycoproteins to construct a chimeric bPIV/hPIV vaccine for use in humans. In another embodiment, the chimeric virions of the present invention may be engineered to create anti-HIV vaccines, wherein an immunogenic polypeptide from gp160, and/or from internal proteins of HIV is engineered into the glycoprotein HN protein to construct a vaccine that is able to elicit both vertebrate humoral and cell-mediated immune responses. In yet another embodiment, the invention relates to recombinant parainfluenza viral vectors and viruses which are engineered to encode mutant parainfluenza viral genes or to encode combinations of genes from different strains of parainfluenza virus.

3.1. Definitions

As used herein, the following terms will have the meanings indicated:
cDNA=complementary DNA
L=large protein
M=matrix protein (lines inside of envelope)
F=fusion glycoprotein
HN=hemagglutinin-neuraminidase glycoprotein
N, NP or NC=nucleoprotein (associated with RNA and required for polymerase activity)
P=phosphoprotein
MOI=multiplicity of infection
NA=neuraminidase (envelope glycoprotein)
PIV=parainfluenza virus
bPIV=bovine parainfluenza virus
hPIV=human parainfluenza virus
bPIV/hPIV=recombinant bPIV with hPIV sequences
nt=nucleotide
RNP=ribonucleoprotein
rRNP=recombinant RNP
vRNA=genomic virus RNA
cRNA=antigenomic virus RNA

4. DESCRIPTION OF FIGURES

FIG. 1. PCR fragments from nt 5255 to nt 6255 derived from three different isolates of the bPIV3/hPIV3 chimeric virus were amplified. The resulting 1 kb DNA fragments were digested with enzymes specific for the F gene of human PIV3. These enzymes do not cut in the corresponding fragment of bovine PIV3. The 1% agarose gel shows the undigested fragment (lanes 2,5, and 6) and the Sac1 or BgIII digested fragments (lanes 4, 6 and lanes 9, 10, and 11, respectively). The sample in lane 10 is undigested, however, upon a repeat of digestion with BgIII, this sample was cut (data not shown). Lanes 1 and 8 show a DNA size marker.

Figure 2:

FIG. 2. PCR fragments from nt 9075 to nt 10469 derived from three different isolates of the bPIV3/hPIV3 chimeric virus were amplified. The resulting 1.4 kb DNA fragments were digested with enzymes specific for the L gene of bovine PIV3. These enzymes do not cut in the corresponding fragment of human PIV3. The 1% agarose gel shows the undigested 1.4 kb fragment (lanes 2, 5, and 8). The smaller DNA fragments produced by digestion with BamH1 and PvuII are shown in lanes 3, 4, 6, 7, 9, and 10). Lane 1 shows a DNA size marker.

5. DESCRIPTION OF THE INVENTION

The present invention relates to recombinant parainfluenza cDNA and RNA constructs including, more specifically, recombinant Kansas strain bovine PIV3 cDNA and RNA constructs, which may be used to express heterologous gene products in appropriate host cell systems and/or to rescue negative strand RNA recombinant viruses that express, package, and/or present the heterologous gene product. These chimeric viruses and expression products may be used as vaccines suitable for administration to humans or animals. In a specific embodiment of the invention, the heterologous gene product is a peptide or protein derived from the genome of a human immunodeficiency virus.

In one embodiment the invention relates to PIV cDNA constructs derived from human or bovine PIV variants, which may be used to express heterologous genes encoding foreign antigens and other products from a variety of pathogens, cellular genes, tumor antigens, and viruses including genes encoding glycoproteins of different species of virus. Thus, the invention encompasses recombinant parainfluenza vectors and viruses which are engineered to encode genes from different species or strains of the parainfluenza virus as well as foreign antigens from pathogens, tumors, allergens, and auto antigens involved in autoimmune disorders. The invention also relates to recombinant parainfluenza viral vectors and viruses which are engineered to encode mutant parainfluenza sequences of the same species or strain.

In a further embodiment, rescue of the chimeric virus or expression products may be achieved by reverse genetics in host cell systems where the host cells are transfected with chimeric cDNA or RNA constructs. The RNA templates of the present are prepared by transcription of appropriate DNA sequences with a DNA-directed RNA polymerase. The RNA templates of the present invention may be prepared either in vitro or in vivo by transcription of appropriate DNA sequences using a DNA-directed RNA polymerase such as bacteriophage T7, T3, the SP6 polymerase or a eukaryotic polymerase such as polymerase I. The resulting RNA templates are of the negative-polarity and contain appropriate terminal sequences which enable the viral RNA-synthesizing apparatus to recognize the template. Alternatively, positive-polarity RNA templates which contain appropriate terminal sequences which enable the viral RNA-synthesizing apparatus to recognize the template, may also be used. Expression from positive polarity RNA templates may be achieved by transfection of plasmids having promoters which are recognized by the DNA-dependent RNA polymerase. For example, plasmid DNA encoding positive RNA templates under the control of a T7 promoter can be used in combination with the vaccinia virus T7 system.

Bicistronic mRNAs can be constructed to permit internal initiation of translation of viral sequences and allow for the expression of foreign protein coding sequences from the regular terminal initiation site, or vice versa. Alternatively, a foreign protein may be expressed from internal transcriptional unit in which the transcriptional unit has an initiation site and polyadenylation site. In another embodiment, the foreign gene is inserted into a PIV gene such that the resulting expressed protein is a fusion protein.

The recombinant mutant parainfluenza viral cDNA and RNA templates of the present invention may be used to transfect transformed cell lines that express the RNA dependent RNA-polymerase and allow for complementation. For example, the recombinant RNA templates may be used to transfect continuous/transfected cell lines that express the RNA-directed RNA polymerase proteins allowing for complementation. In a preferred embodiment, a non-virus dependent replication system is used to recover chimeric PIV, in which plasmid DNA encoding the PIV genome or antigenome is coexpressed with plasmid DNA encoding the minimum subset of PIV proteins needed for specific replication and expression of the virus, as demonstrated by way of working example as described infra.

Alternatively, a plasmid expressing from an appropriate promoter, can be used for virus specific (chimeric) cDNA or RNA transfection. Complementation may also be achieved with the use of a helper virus which provides the RNA dependent RNA-polymerase. Additionally, a non-virus dependent replication system for parainfluenza virus is also described. The minimum subset of parainfluenza virus proteins needed for specific replication and expression of the virus are the three proteins, L, P, and N or NP, which can be expressed from plasmids by a vaccinia virus T7 or other system.

The expression products and/or chimeric virions obtained may advantageously be utilized in vaccine formulations. The expression products and chimeric virions of the present invention may be engineered to create vaccines against a broad range of pathogens, including viral and bacterial antigens, tumor antigens, allergen antigens, and auto antigens involved in autoimmune disorders. In particular, the chimeric virions of the present invention may be engineered to create anti-human parainfluenza vaccines, wherein the bovine parainfluenza fusion (F) and hemagglutinin (HN) glycoproteins are replaced by the human F and HN glycoproteins to construct a chimeric bPIV/hPIV vaccine for use in humans. In another embodiment, the chimeric virions of the present invention may be engineered to create anti-HIV vaccines, wherein an immunogenic polypeptide from gp160, and/or from internal proteins of HIV is engineered into the glycoprotein HN protein to construct a vaccine that is able to elicit both vertebrate humoral and cell-mediated immune responses. In yet another embodiment, the invention relates to recombinant parainfluenza viral vectors and viruses which are engineered to encode mutant parainfluenza viral genes or to encode combinations of genes from different strains of parainfluenza virus.

In a broader embodiment, the expression products and chimeric virions of the present invention may be engineered to create vaccines against a broad range of pathogens, including viral antigens, tumor antigens and auto antigens involved in autoimmune disorders. One way to achieve this goal involves modifying existing PIV genes to contain foreign sequences in their respective external domains.

Where the heterologous sequences are epitopes or antigens of pathogens, these chimeric viruses may be used to induce a protective immune response against the disease agent from which these determinants are derived.

Thus, the present invention relates to the use of viral vectors and chimeric viruses to formulate vaccines against a broad range of viruses and/or antigens including tumor antigens. The viral vectors and chimeric viruses of the present invention may be used to modulate a subject's immune system by stimulating a humoral immune response, a cellular immune response or by stimulating tolerance to an antigen. As used herein, a subject means: humans, primates, horses, cows, sheep, pigs, goats, dogs, cats, avian species and rodents. When delivering tumor antigens, the invention may be used to treat subjects having disease amenable to immunity mediated rejection, such as non-solid tumors or solid tumors of small size. It is also contemplated that delivery of tumor antigens by the viral vectors and chimeric viruses described herein will be useful for treatment subsequent to removal of large solid tumors. The invention may also be used to treat subjects who are suspected of having cancer.

The invention may be divided into the following stages solely for the purpose of description and not by way of limitation: (a) construction of recombinant cDNA and RNA templates; (b) expression of heterologous gene products using recombinant cDNA and RNA templates; and (c) rescue of the heterologous gene in recombinant virus particles.

5.1. Construction of the Recombinant cDNA and RNA

A specific embodiment of the present invention is a chimeric virus comprising a backbone encoded by nucleotide sequences derived from bovine parainfluenza virus genome, such as the Kansas strain of bPIV3, in which bovine parainfluenza virus nucleotide sequences have been substituted with heterologous sequences or in which heterologous sequences have been added to the complete bPIV genome. The present invention also encompasses chimeric viruses comprising a backbone encoded by nucleotide sequences derived from a bPIV genome containing mutations or modifications, in addition to heterologous sequences, which result in a chimeric virus having a phenotype more suitable for use in vaccine formulations, e.g., attenuated phenotype or enhanced antigenicity. In accordance with this particular embodiment of the invention, a heterologous sequence in the context of a bovine PIV3 backbone may be any sequence heterologous to bPIV3.

Another specific emodiment of the present invention is a chimeric virus comprising a backbone encoded by nucleotide sequences derived from human PIV 1, 2, or 3 in which hPIV nucleotide sequences have been substituted with heterologous sequences or in which heterologous sequences have been added to the complete hPIV genome, with the proviso that the resulting chimeric virus is not a chimeric hPIV3 in which the hemagglutinin-neuraminidase and fusion glycoproteins have been replaced by those of hPIV1. The present invention also encompasses chimeric viruses comprising a backbone encoded by nucleotide sequences derived from a hPIV genome containing mutations or modifications, in addition to heterologous sequences, which result in a chimeric virus having a phenotype more suitable for use in vaccine formulations, e.g., attenuated phenotype or enhanced antigenicity.

Heterologous gene coding sequences flanked by the complement of the viral polymerase binding site/promoter, e.g. the complement of 3'-PIV virus terminus of the present invention, or the complements of both the 3'- and 5'-PIV virus termini may be constructed using techniques known in the art. The resulting RNA templates may be of the negative-polarity and contain appropriate terminal sequences which enable the viral RNA-synthesizing apparatus to recognize the template. Alternatively, positive-polarity RNA templates which contain appropriate terminal sequences which enable the viral RNA-synthesizing apparatus to recognize the template, may also be used. Recombinant DNA molecules containing these hybrid sequences can be cloned and transcribed by a DNA-directed RNA polymerase, such as bacteriophage T7, T3, the SP6 polymerase or eukaryotic polymerase such as polymerase I and the like, to produce in vitro or in vivo the recombinant RNA templates which possess the appropriate viral sequences that allow for viral polymerase recognition and activity.

In accordance with the present invention, heterologous sequences which may be constructed into the chimeric viruses of the invention include: 1) antigens that are characteristic of a pathogen such as bacteria and viruses; 2) antigens that are characteristic of autoimmune disease; 3) antigens that are characteristic of an allergen; and 4) antigens that are characteristic of a tumor.

In a preferred embodiment, heterologous gene sequences that can be expressed into the chimeric viruses of the invention include but are not limited to antigenic epitopes and glycoproteins of viruses which result in respiratory disease, such as influenza glycoproteins, in particular hemagglutinin H5, H7, respiratory syncytial virus epitopes, New Castle Disease virus epitopes, Sendai virus and infectious Laryngotracheitis virus (ILV). In yet another embodiment of the invention, heterologous gene sequences that can be engineered into the chimeric viruses of the invention include, but are not limited to, viral epitopes and glycoproteins of viruses, such as hepatitis B virus surface antigen, hepatitis A or C virus surface glycoproteins of Epstein Barr virus, glycoproteins of human papilloma virus, simian virus 5 or mumps virus, glycoproteins of herpes virus, VPI of poliovirus, and sequences derived from a human immunodeficiency virus (HIV), preferably type 1 or type 2. In yet another embodiment, heterologous gene sequences that can be engineered into chimeric viruses of the invention include, but are not limited to, Marek's Disease virus (MDV) epitopes, epitopes of infectious Bursal Disease virus (IBDV), epitopes of Chicken Anemia virus, infectious laryngotracheitis virus (LV), Avian Influenza virus (AIV), rabies, feline leukemia virus, canine distemper virus, vesicular stomatitis virus, and swinepox virus (see Fields et al. (ed.), 1991, *Fundamental Virology, Second Edition* Raven Press, New York, incorporated by reference herein in its entirety).

Other heterologous sequences of the present invention include antigens that are characteristic of autoimmune disease. These antigens will typically be derived from the cell surface, cytoplasm, nucleus, mitochondria and the like of mammalian tissues, including antigens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discold lupus erythromatosus.

Antigens that are allergens generally include proteins or glycoproteins, including antigens derived from pollens, dust, molds, spores, dander, insects and foods. In addition, antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within a PIV gene coding sequence such that a chimeric gene product is expressed which contains the heterologous peptide sequence within the PIV viral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

In yet another embodiment, heterologous gene sequences that can be engineered into the chimeric viruses include those that encode proteins with immunopotentiating activities. Examples of immunopotentiating proteins include, but are not limited to, cytokines, interferon type 1, gamma interferon, colony stimulating factors, and interleukin-1, -2, -4, -5, -6, -12.

In addition, other heterologous gene sequences that may be engineered into the chimeric viruses include antigens derived from bacteria such as bacterial surface glycoproteins, antigens derived from fungi, and antigens derived from a variety of other pathogens and parasites. Examples of heterologous gene sequences derived from bacterial pathogens include, but are not limited to, antigens derived from species of the following genera: *Salmonella, Shigella, Chlamydia, Helicobacter, Yersinia, Bordatella, Pseudomonas, Neisseria, Vibrio, Haemophilus, Mycoplasma, Streptomyces, Treponema, Coxiella, Ehrlichia, Brucella, Streptobacillus, Fusospirocheta, Spirillum, Ureaplasma, Spirochaeta, Mycoplasma, Actinomycetes, Borrelia, Bacteroides, Trichomoras, Branhamella, Pasteurella, Clostridium, Corynebacterium, Listeria, Bacillus, Erysipelothrix, Rhodococcus, Escherichia, Klebsiella, Pseudomanas, Enterobacter, Serratia, Staphylococcus, Streptococcus, Legionella, Mycobacterium, Proteus, Campylobacter, Enterococcus, Acinetobacter, Morganella, Moraxella, Citrobacter, Rickettsia, Rochlimeae*, as well as bacterial species such as: *P. aeruginosa; E. coli P. cepacia, S. epidermis, E. faecalis, S. neumonias, S. aureus, N. meningitidis, S. pyogenes, Pasteurella multocida, Treponema pallidum*, and *P. mirabilis.*

Examples of heterologous gene sequences derived from pathogenic fungi, include, but are not limited to, antigens derived from fungi such as *Cryptococcus neoformans; Blastomyces dermatitidis; Aiellomyces dermatitidis; Histoplasma capsulatum; Coccidioides immitis; Candida* species, including *C albicans, C tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata; Trichophyton* species, *Microsporum* species and *Dermatophyres* species, as well as any other yeast or fungus now known or later identified to be pathogenic.

Finally, examples of heterologous gene sequences derived from parasites include, but are not limited to, antigens derived from members of the Apicomplexa phylum such as, for example, *Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus* and *Gregarina* spp.; *Pneumocystis carinii*; members of the Microspora phylum such as, for example, *Nosema, Enterocytozoon, Encephalitozoon, Septata, Mrazekia, Amblyospora, Ameson, Glugea, Pleistophora* and *Microsporidium* spp.; and members of the Ascetospora phylum such as, for example, *Haplosporidium* spp., as well as species including *Plasmodium falciparum, P. vivax, P. ovale, P. malaria; Toxoplasma gondii; Leishmania mexicana, L. tropica, L. major, L. aethiopica, L. donovani, Trypanosoma cruzi, T. brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T. saginata, Trichomonas vaginatis, T. hominis, T. tenax; Giardia lamblia; Cryptosporidium parvum; Pneumocytis carinii, Babesia bovis, B. divergens, B. microti, Isospora belli, L hominis; Dientamoeba fragilis; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchisfelineas, G. Viverini, Fasciola hepatica, Sarcoptes scabiei, Pediculus humanus; Phthirlus pubis*; and *Dermatobia hominis*, as well as any other parasite now known or later identified to be pathogenic.

One approach for constructing these hybrid molecules is to insert the heterologous coding sequence into a DNA complement of a PIV gene so that the heterologous sequence is flanked by the viral sequences required for viral polymerase activity; i.e., the viral polymerase binding site/promoter, hereinafter referred to as the viral polymerase binding site, and a polyadenylation site. In a preferred embodiment, the heterologous coding sequence is flanked by the viral sequences that comprise the replication promoters of the 5' and 3' termini, the gene start and gene end sequences, and the packaging signals that are found in the 5' and/or the 3' termini. In an alternative approach, oligonucleotides encoding the viral polymerase binding site, e.g., the complement of the 3'-terminus or both termini of the virus genomic segment can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82; 488). Variations in polymerase chain reaction (PCR) technology, described infra, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophage T3, T7 or SP6) and the hybrid sequence containing the heterologous gene and the PIV polymerase binding site. RNA templates could then be transcribed directly from this recombinant DNA. In yet another embodiment, the recombinant RNA templates may be prepared by ligating RNAs specifying the negative polarity of the heterologous gene and the viral polymerase binding site using an RNA ligase.

In addition, one or more nucleotides can be added at the 3' end of the HN gene in the untranslated region to adhere to the "Rule of Six" which may be important in obtaining virus rescue. The "Rule of Six" applies to many paramyxoviruses and states that the RNA nucleotide genome must be divisible by six to be functional. The addition of nucleotides can be accomplished by techniques known in the art such as using a commercial mutagenesis kits such as the QuikChange mutagenesis kit (Stratagene), After addition of the appropriate number of nucleotides, the correct hPIV3 F and HN gene DNA fragment can then be isolated by digestion with appropriate restriction enzyme and gel purification. Sequence requirements for viral polymerase activity and constructs which may be used in accordance with the invention are described in the subsections below.

5.1.1. Insertion of the Heterologous Gene Sequence

Insertion of a foreign gene sequence into the nonsegmented genome of PIV can be accomplished by either a complete replacement of a viral coding region with a foreign gene or by a partial replacement. Complete replacement would probably best be accomplished through the use of PCR-directed mutagenesis. Briefly, PCR-primer A would contain, from the 5' to 3' end: a unique restriction enzyme site, such as a class IIS restriction enzyme site (i.e., a "shifter" enzyme; that recognizes a specific sequence but cleaves the DNA either upstream or downstream of that sequence); a stretch of nucleotides complementary to a region of the PIV gene; and a stretch of nucleotides complementary to the carboxy-terminus coding portion of the foreign gene product. PCR-primer B would contain from the 5' to 3' end: a unique restriction enzyme site; a stretch of nucleotides complementary to a PIV gene; and a stretch of nucleotides corresponding to the 5' coding portion of the foreign gene. After a PCR reaction using these primers with a cloned copy of the foreign gene, the product may be excised and cloned using the unique restriction sites. Digestion with the class IIS enzyme and transcription with the purified phage polymerase would generate an RNA molecule containing the exact untranslated ends of the PIV gene with a foreign gene insertion. In an alternate embodiment, PCR-primed reactions could be used to prepare double-stranded DNA containing the bacteriophage promoter sequence, and the hybrid gene sequence so that RNA templates can be transcribed directly without cloning.

5.1.2. Insertion of the Heterologous Gene Sequence into the HN Gene

The hemagglutinin and neuraminidase activities of PIV are coded for by a single gene, HN. The HN protein is a major surface glycoprotein of the virus. For a variety of viruses, such as parainfluenza, the hemagglutinin and neuraminidase proteins have been demonstrated to contain a number of antigenic sites. Consequently, this protein is a potential target for the humoral immune response after infection. Therefore, substitution of antigenic sites within HN with a portion of a foreign protein may provide for a vigorous humoral response against this foreign peptide. If a sequence is inserted within the HN molecule and it is expressed on the outside surface of the HN it will be immunogenic. For example, a peptide derived from gp160 of HIV could replace an antigenic site of the HN protein, resulting in the elicitation of both a humoral immune response. In a different approach, the foreign peptide sequence may be inserted within the antigenic site without deleting any viral sequences. Expression products of such constructs may be useful in vaccines against the foreign antigen, and may indeed circumvent a problem discussed earlier, that of propagation of the recombinant virus in the vaccinated host. An intact HN molecule with a substitution only in antigenic sites may allow for HN function and thus allow for the construction of a viable virus. Therefore, this virus can be grown without the need for additional helper functions. The virus may also be attenuated in other ways to avoid any danger of accidental escape.

Other hybrid constructions may be made to express proteins on the cell surface or enable them to be released from the cell. As a surface glycoprotein, the HN has an amino-terminal cleavable signal sequence necessary for transport to the cell surface, and a carboxy-terminal sequence necessary for membrane anchoring. In order to express an intact foreign protein on the cell surface it may be necessary to use these HN signals to create a hybrid protein. In this case, the fusion protein may be expressed as a separate fusion protein from an additional internal promoter. Alternatively, if only the transport signals are present and the membrane anchoring domain is absent, the protein may be secreted out of the cell.

5.1.3. Construction of Bicistronic RNA

Bicistronic mRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with parainfluenza packaging limitations. Thus, it is preferable that the IRES chosen for such a bicistronic approach be no more than 500 nucleotides in length, with less than 250 nucleotides being preferred. Further, it is preferable that the IRES utilized not share sequence or structural homology-with picornaviral elements. Preferred IRES elements include, but are not limited to the mammalian BiP IRES and the hepatitis C virus IRES.

Alternatively, a foreign protein may be expressed from a new internal transcriptional unit in which the transcriptional unit has an initiation site and polyadenylation site. In another embodiment, the foreign gene is inserted into a PIV gene such that the resulting expressed protein is a fusion protein.

5.2. Expression of Heterologous Gene Products Using Recombinant cDNA and RNA Templates The recombinant templates prepared as described above can be used in a variety of ways to express the heterologous gene products in appropriate host cells or to create chimeric viruses that express the heterologous gene products. In one embodiment, the recombinant cDNA can be used to transfect appropriate host cells and the resulting RNA may direct the expression of the heterologous gene product at high levels. Host cell systems which provide for high levels of expression include continuous cell lines that supply viral functions such as cell lines superinfected with PIV, cell lines engineered to complement PIV functions, etc.

In an alternate embodiment of the invention, the recombinant templates may be used to transfect cell lines that express a viral polymerase protein in order to achieve expression of the heterologous gene product. To this end, transformed cell lines that express a polymerase protein such as the L protein may be utilized as appropriate host cells. Host cells may be similarly engineered to provide other viral functions or additional functions such as HN, NP or N.

In another embodiment, a helper virus may provide the RNA polymerase protein utilized by the cells in order to achieve expression of the heterologous gene product. In yet another embodiment, cells may be transfected with vectors encoding viral proteins such as the N or NP, P and L proteins.

5.3. Rescue of Recombinant Virus Particles

In order to prepare chimeric virus, modified cDNAs, virus RNAs, or RNA coding for the PIV genome and/or foreign proteins in the plus or minus sense may be used to transfect cells which provide viral proteins and functions required for replication and rescue. Alternatively, cells may be transfected with helper virus before, during, or after transfection by the DNA or RNA molecule coding for the PIV genome and/or foreign proteins. The synthetic recombinant plasmid PIV DNAs and RNAs can be replicated and rescued into infectious virus particles by any number of techniques known in the art, as described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

In one embodiment, of the present invention, synthetic recombinant viral RNAs may be prepared that contain the non-coding regions of the negative strand virus RNA which are essential for the recognition by viral polymerases and for packaging signals necessary to generate a mature virion. There are a number of different approaches which may be used to apply the reverse genetics approach to rescue negative strand RNA viruses. First, the recombinant RNAs are synthesized from a recombinant DNA template and reconstituted in vitro with purified viral polymerase complex to form recombinant ribonucleoproteins (RNPs) which can be used to transfect cells. In another approach, a more efficient transfection is achieved if the viral polymerase proteins are present during transcription of the synthetic RNAs either in vitro or in vivo. With this approach the synthetic RNAs may be transcribed from cDNA plasmids which are either co-transcribed in vitro with cDNA plasmids encoding the polymerase proteins, or transcribed in vivo in the presence of polymerase proteins, i.e., in cells which transiently or constitutively express the polymerase proteins.

In additional approaches described herein, the production of infectious chimeric virus may be replicated in host cell systems that express a PIV viral polymerase protein (e.g., in virus/host cell expression systems; transformed cell lines engineered to express a polymerase protein, etc.), so that infectious chimeric virus are rescued. In this instance, helper virus need not be utilized since this function is provided by the viral polymerase proteins expressed.

In accordance with the present invention, any technique known to those of skill in the art may be used to achieve replication and rescue of chimeric viruses. One approach involves supplying viral proteins and functions required for replication in vitro prior to transfecting host cells. In such an embodiment, viral proteins may be supplied in the form of wildtype virus, helper virus, purified viral proteins or recombinantly expressed viral proteins. The viral proteins may be supplied prior to, during or post transcription of the synthetic cDNAs or RNAs encoding the chimeric virus. The entire mixture may be used to transfect host cells. In another approach, viral proteins and functions required for replication may be supplied prior to or during transcription of the synthetic cDNAs or RNAs encoding the chimeric virus. In such an embodiment, viral proteins and functions required for replication are supplied in the form of wildtype virus, helper virus, viral extracts, synthetic cDNAs or RNAs which express the viral proteins are introduced into the host cell via infection or transfection. This infection/transfection takes place prior to or simultaneous to the introduction of the synthetic cDNAs or RNAs encoding the chimeric virus.

In a particularly desirable approach, cells engineered to express all PIV viral genes may result in the production of infectious chimeric virus which contain the desired genotype; thus eliminating the need for a selection system. Theoretically, one can replace any one of the six genes or part of any one of the six genes encoding structural proteins of PIV with a foreign sequence. However, a necessary part of this equation is the ability to propagate the defective virus (defective because a normal viral gene product is missing or altered). A number of possible approaches exist to circumvent this problem. In one approach a virus having a mutant protein can be grown in cell lines which are constructed to constitutively express the wild type version of the same protein. By this way, the cell line complements the mutation in the virus. Similar techniques may be used to construct transformed cell lines that constitutively express any of the PIV genes. These cell lines which are made to express the viral protein may be used to complement the defect in the recombinant virus and thereby propagate it. Alternatively, certain natural host range systems may be available to propagate recombinant virus.

In yet another embodiment, viral proteins and functions required for replication may be supplied as genetic material in the form of synthetic cDNAs or RNAs so that they are co-transcribed with the synthetic cDNAs or RNAs encoding the chimeric virus. In a particularly desirable approach, plasmids which express the chimeric virus and the viral polymerase and/or other viral functions are co-transfected into host cells. For example, plasmids encoding the genomic or antigenomic PIV RNA, either wild type or modified, may be co-transfected into host cells with plasmids encoding the PIV viral polymerase proteins NP or N, P or L. Alternatively, rescue of chimeric PIV3/PIV3 virus may be accomplished by the use of Modified Vaccinia Virus Ankara (MVA), or a combination of MVA and plasmids encoding the polymerase proteins. For example, MVA can be transfected into HeLa or Vero cells. After infection with MVA, a full length antigenomic bPIV3/hPIV3 cDNA may be transfected into the HeLa or Vero cells together with the NP, P, and L encoding expression plasmids. The cells and cell supernatant can subsequently be harvested and subjected to a single freeze-thaw cycle. The resulting cell lysate may then be used to infect a fresh HeLa or Vero cell monolayer in the presence of 1-beta-D-arabinofuranosylcytosine (ara C), a replication inhibitor of vaccinia virus, to generate a virus stock. The supernatant and cells from these plates can then be harvested, freeze-thawed once and the presence of bPIV3 virus particles assayed for by immunostaining of virus plaques using PIV3-specific antiserum.

Another approach to propagating the recombinant virus may involve co-cultivation with wild-type virus. This could be done by simply taking recombinant virus and co-infecting cells with this and another wild-type virus (preferably a vaccine strain). The wild-type virus should complement for the defective virus gene product and allow growth of both the wild-type and recombinant virus. Alternatively, a helper virus may be used to support propagation of the recombinant virus.

In another approach, synthetic templates may be replicated in cells co-infected with recombinant viruses that express the PIV virus polymerase protein. In fact, this method may be used to rescue recombinant infectious virus in accordance with the invention. To this end, the PIV polymerase protein may be expressed in any expression vector/host cell system, including but not limited to viral expression vectors (e.g., vaccinia virus, adenovirus, baculovirus, etc.) or cell lines that express a polymerase protein (e.g., see Krystal et al., 1986, Proc. Natl. Acad. Sci. USA 83: 2709-2713). Moreover, infection of host cells expressing all six PIV proteins may result in the production of infectious chimeric virus particles. This system would eliminate the need for a selection system, as all recombinant virus produced would be of the desired genotype. It should be noted that it may be possible to construct a recombinant virus without altering virus viability. These altered viruses would then be growth competent and would not need helper functions to replicate.

5.4. Vaccine Formulations Using the Chimeric Viruses

The invention encompasses vaccine formulations comprising the engineered negative strand RNA virus of the present invention. The recombinant PIV viruses of the present invention may be used as a vehicle to express foreign epitopes that induce a protective response to any of a variety of pathogens. In a specific embodiment, the invention encompasses the use of recombinant bPIV viruses which have been modified in vaccine formulations to confer protection against hPIV infection.

The invention encompasses vaccine formulations to be administered to humans and animals which are useful to protect against PIV, influenza, RSV, Sendai virus, mumps, laryngotracheitis virus, simianvirus 5, human papillomavirus, as well as other viruses and pathogens.

In one embodiment, the invention encompasses vaccine formulations which are useful against domestic animal disease causing agents including rabies virus; feline leukemia virus (FLV) and canine distemper virus. In yet another embodiment, the invention encompasses vaccine formulations which are useful to protect livestock against vesicular stomatitis virus, rabies virus, rinderpest virus, swinepox virus, and further, to protect wild animals against rabies virus.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain. For example, antigens of non-related viruses such as HIV (gp160, gp120, gp41) parasite antigens (e.g., malaria), bacterial or fungal antigens or tumor antigens can be engineered into the attenuated strain. Alternatively, epitopes which alter the tropism of the virus in vivo can be engineered into the chimeric attenuated viruses of the invention.

Virtually any heterologous gene sequence may be constructed into the chimeric viruses of the invention for use in vaccines. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to influenza and parainfluenza hemagglutinin neuraminidase and fusion glycoproteins such as the HN and F genes of human PIV3. In yet another embodiment, heterologous gene sequences that can be engineered into the chimeric viruses include those that encode proteins with immunopotentiating activities. Examples of immunopotentiating proteins include, but are not limited to, cytokines, interferon type 1, gamma interferon, colony stimulating factors, interleukin-1, -2, -4, -5, -6, -12.

In addition, heterologous gene sequences that can be constructed into the chimeric viruses of the invention for use in vaccines include but are not limited to sequences derived from a human immunodeficiency virus (HIV), preferably type 1 or type 2. In a preferred embodiment, an immunogenic HIV-derived peptide which may be the source of an antigen may be constructed into a chimeric PIV that may then be used to elicit a vertebrate immune response. Such HIV-derived peptides may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25), tat, rev, nef, vif, vpu, vpr, and/or vpx.

Other heterologous sequences may be derived from hepatitis B virus surface antigen (HBsAg); hepatitis A or C virus surface antigens, the glycoproteins of Epstein Barr virus; the glycoproteins of human papillomavirus; the glycoproteins of respiratory syncytial virus, parainfluenza virus, Sendai virus, simianvirus 5 or mumps virus; the glycoproteins of influenza virus; the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Other heterologous sequences may be derived from tumor antigens, and the resulting chimeric viruses be used to generate an immune response against the tumor cells leading to tumor regression in vivo. These vaccines may be used in combination with other therapeutic regimens, including but not limited to chemotherapy, radiation therapy, surgery, bone marrow transplantation, etc. for the treatment of tumors. In accordance with the present invention, recombinant viruses may be engineered to express tumor-associated antigens (TAAs), including but not limited to, human tumor antigens recognized by T cells (Robbins and Kawakami, 1996, Curr. Opin. Immunol. 8:628-636, incorporated herein by reference in its entirety), melanocyte lineage proteins, including gp100, MART-1/MelanA, TRP-1 (gp75), tyrosinase; Tumor-specific widely shared antigens, MAGE-1, MAGE-3, BAGE, GAGE-1, GAGE-1, N-acetylglucosaminyltransferase-V, p15; Tumor-specific mutated antigens, β-catenin, MUM-1, CDK4; Nonmelanoma antigens for breast, ovarian, cervical and pancreatic carcinoma, HER-2/neu, human papillomavirus-E6, -E7, MUC-1.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification. Additionally, as bPIV has been demonstrated to be non-pathogenic in humans, this virus is highly suited for use as a live vaccine.

In this regard, the use of genetically engineered PIV (vectors) for vaccine purposes may desire the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication within the host. When used as a vaccine, the recombinant virus would go through limited replication cycle(s) and induce a sufficient level of immune response but it would not go further in the human host and cause disease. Recombinant viruses lacking one or more of the PIV genes or possessing mutated PIV genes would not be able to undergo successive rounds of replication. Defective viruses can be produced in cell lines which permanently express such a gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion.

The advantage of such preparations is that they contain native proteins and do not undergo inactivation by treatment with formalin or other agents used in the manufacturing of killed virus vaccines. Alternatively, mutated PIV made from cDNA may be highly attenuated so that it replicates for only a few rounds.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and *Corynebacterium parvum*.

Many methods may be used to introduce the vaccine formulations described above, these include but are not limited to oral, intradermal, intramuscular, intraperitoneal, intravenous, subcutaneous, and intranasal routes. It may be preferable to introduce the chimeric virus vaccine formulation via the natural route of infection of the pathogen for which the vaccine is designed.

6. EXAMPLE 1

Construction and Cloning of Chimeric Bovine Parainfluenza 3/Human Parainfluenza 3 cDNA For the purpose of interchanging the F and HN genes of bPIV3 with those of hPIV3, additional restriction enzyme sites were introduced into the infectious bPIV3 cDNA. Using site-directed mutagenesis, a unique Nhe 1 site was introduced at nucleotide position 5041 and a Sal 1 site was introduced at nt 8529 in the bPIV3 cDNA. The modified full-length bPIV3 cDNA was treated with Nhe 1 and Sal 1 and a ~14 kb DNA fragment encompassing all of the viral bPIV3 sequences except the F and HN genes, was isolated by gel purification.

To obtain the hPIV3 F and HN gene sequences, a 10 cm dish of confluent Vero cells was infected with hPIV3/Tex/12084/1983. After 3 days of incubation at 37° C., the cells were harvested and total RNA was isolated using RNA STAT-LS 50 (Tel-Test Inc.). Viral cDNA was generated by reverse transcription using a hPIV3 specific oligo annealing at position 4828 of the hPIV3 genome. The hPIV3 F and HN genes were amplified by PCR (polymerase chain reaction) using Taq polymerase. The PCR product was cloned into the pT/A TOPO cloning vector (Invitrogen) and from two clones (#11 and #14) the hPIV3 F and HN genes were sequenced. In the sequence revealed for clone #11, the F gene was correct, but the HN gene contained aberrant sequences. While for the second clone #14, the HN gene was correct, but the F gene contained aberrant stop codons. Thus, a functional hPIV3 F and HN genes-containing plasmid was constructed by combining the correct F gene of #11 with the correct HN gene of #14 in the following manner. Both hPIV3 plasmids (#11 and #14) were digested with Nhe1 and EcoR1. A 1.6 kb fragment harboring the correct F gene was isolated from clone #11 and a 8.5 kb fragment containing the correct HN gene and plasmid sequences, was isolated from clone #14. The two fragments were ligated to produce the intact hPIV3 F and HN genes-containing plasmid. The correct sequence was confirmed by DNA sequence analysis. Finally, a single nucleotide was added at the 3' end of the HN gene in the untranslated region to adhere to the "Rule of Six." The addition of the single nucleotide was accomplished by using the QuikChange mutagenesis kit (Stratagene) and was confirmed by DNA sequencing. The correct hPIV3 F and HN gene DNA fragment was then isolated by digestion with Nhe 1 and Sal 1 and a 3.5 kb DNA fragment was gel purified.

The full-length bPIV3/hPIV3 chimeric cDNA was constructed by ligating the 14.5 kb DNA fragment harboring bPIV3 sequences described above and the 3.5 kb DNA fragment containing the hPIV3 F and HN genes (see FIG. 1). The full-length chimeric plasmid DNA was confirmed by extensive restriction enzyme mapping. In addition, the M/F and HN/L gene junctions of the chimeric construct were confirmed by DNA sequencing to both contain bPIV3 and hPIV3 sequences as well as a Nhe 1 and a Sal 1 restriction enzyme site, respectively.

7. EXAMPLE 2

Rescue of Chimeric Bovine Parainfluenza Type 3/Human Parainfluenza Type 3 Virus in Hela Cells and Vero Cells Rescue of the chimeric bPIV3/hPIV3 virus was done using a similar procedure as for bPIV3 rescue. Rescue of bPIV3/hPIV3 chimeric virus by reverse genetics was carried out in HeLa cells using LipofecTACE (Gibco/BRL). The 80% confluent HeLa cells or Vero cells were infected with MVA at an MOI of 4. One hour post-infection, the full-length anti-genomic bPIV3/hPIV3 cDNA (4 µg) was transfected into the infected HeLa or Vero cells together with the NP (0.4 µg), P (0.4 µg), and L/pCITE (0.2 µg) expression plasmids. Forty hours post-transfection, the cells and the cell supernatant were harvested (P0) and subjected to a single freeze-thaw cycle. The resulting cell lysate was then used to infect a fresh Vero cell monolayer in the presence of 1-beta-D-arabinofuranosylcytosine (ara C), a replication inhibitor of vaccinia virus, to generate a P1 virus stock. The supernatant and cells from these plates were harvested, freeze-thawed once and the presence of bPIV3 virus particles was assayed for by immunostaining of virus plaques using PIV3-specific antiserum. The cell lysates of the P1 harvest resulted in complete CPE of the Vero cell monolayers and immunostaining indicated the presence of an extensive virus infection.

8. EXAMPLE 3

Confirmation of Chimeric Bovine Parainfluenza Type 3/Human Parainfluenza Type 3 Virus Rescue by RT-PCR To ascertain that the rescued virus is chimeric in nature, i.e. the virus contains hPIV3 F and HN gene sequences in a bPIV3 backbone, the viral RNA genome was analyzed further by RT-PCR. Vero cells, infected with the P1 virus stock of three independently derived isolates of bPIV3/hPIV3 were harvested and total RNA was isolated. The viral RNA was amplified using an oligo that anneals at position 4757 of bPIV3. A viral region from nt 5255 to 6255 was amplified by PCR The resulting 1 kb PCR fragment should contain bPIV3 sequences. This was confirmed by digestion with enzymes (Sac1 and Bg1 II) specific for hPIV3 and that do not cut in the complementary region of bPIV3 (see FIG. 1). As expected, Sac1 and Bg1 II cut the PCR fragment into smaller fragments confirming that the isolated sequences are derived from hPIV3 (see lanes 3, 5, 7). In addition, a region in the polymerase L gene from nt 9075 to nt 10469 was amplified by PCR. This region should contain bPIV3 sequences. Again the resulting 1.4 kb PCR fragment was digested using enzyme specific for bPIV3 (Pvull and BamH1) that do not cut in the equivalent region of hPIV3 (FIG. 2). The 1.4 kb fragment was indeed digested by both Pvull and BamH1 confirming that the polymerase gene is bPIV3 in origin (see lanes 3, 4, 6, 7, 9 and 10 of FIG. 2). In summary, the RT-PCR analysis shows that the rescued bPIV3/hPIV3 virus is chimeric in nature. It contains hPIV3 F and HN genes in a bPIV3 genetic backbone.

9. EXAMPLE 4

The Chimeric Bovine PIV Demonstrate Attenuated Phenotypes and Elicit Strong Protective Responses when Administered In Vivo Five week old Syrian Golden hamsters were infected with $5 \times 10^5$ pfu of wildtype bPIV3, recombinant bPIV3, hPIV3, human/bovine PIV3, and placebo. The five different animal groups were kept separate in micro-isolator cages. Four days post-infection, the animals were sacrificed. The nasal turbinates and lungs of the animals were homogenized and stored at −80° C. Virus present in the tissues was determined by $TCID_{50}$ assays in MDBK cells at 37° C. Virus infection was confirmed by hemabsorption with guinea pig red blood cells. Table 1 shows the replication titers of the different PIV3 strains in hamsters in the lungs and nasal turbinates. Note that recombinant bPIV3 and the bPIV3/hPIV3 chimeric viruses are attenuated in the lungs of the hamsters:

TABLE 1

Replication of PIV3 Viruses in Syrian Golden Hamsters in the Nasal Turbinates and Lungs.

| Virus Used to Infect the Animals | Nasal Turbinates $Log_{10}$ $TCID_{50}$/g tissue | Lungs $Log_{10}$ $TCID_{50}$/g tissue |
|---|---|---|
| Wild type bPIV3 | 5.47 +/− 0.001 | 5.22 +/− 0.014 |
| Recombinant bPIV3 | 5.00 +/− 0.361 | 2.90 +/− 0.490 |
| Wild type hPIV3 | 4.86 +/− 0.072 | 4.81 +/− 0.123 |
| BPIV3/h PIV3 chimeric virus | 4.68 +/− 0.104 | 3.73 +/− 0.418 |
| Placebo | 0 | 0 |

Furthermore, serum samples collected from the hamsters prior to infection and at day 21 post-infection were analyzed in a hemagglutination inhibition assay. The serum samples were treated with receptor destroying enzyme (RDE, DENKA Seiken Co.) and non-specific agglutinins were removed by incubation with guinea pig red blood cells for 1 hour on ice. Wildtype bPIV3 and hPIV3 were added to two-fold serially diluted hamster serum samples. Finally, guinea pig red blood cells (0.5%) were added, and hemagglutination was allowed to occur at room temperature. Table 2 shows the antibody response generated in the hamsters upon being infected with the different PIV3 strains. Note that the bPIV3/hPIV3 chimeric virus generates as strong an antibody response against hPIV3 as does wild type hPIV3, far exceeding the response generated by the recombinant or wildtype bPIV3:

TABLE 2

Hemaglutination Inhibition Assay Using Serum from Hamsters Infected with Different PIV3 Viruses.

| Virus Used for Inoculation of the Hamsters | Hamster Serum Titers for | |
|---|---|---|
| | wt bPIV3 | HPIV3 |
| Recombinant bPIV3 | 1:16 | 1:16 |
| Wt bPIV3 | 1:16 | 1:8 |
| Wt hPIV3 | 1:4 | 1:128 |
| bPIV3/hPIV3 chimeric virus | 1:8 | 1:128 |
| Placebo | <1:4 | <1.4 |

These results demonstrate the properties of bPIV3/hPIV3 chimeric viruses of the present invention which make these recombinants suitable for use in vaccine formulations. Not only do the bPIV3/hPIV3 chimeric viruses demonstrate an attenuated phenotype when administered in vivo, but they also generate as strong an antibody response as the wildtype hPIV3. Thus, because the chimeric viruses of the present invention have a unique combination of having an attenuated phenotype and eliciting as strong an immune response as a wildtype hPIV, these chimeric viruses have the characteristics necessary for successful use in humans to inhibit and/or protect against infection with PIV.

10. EXAMPLE 5

Construction of a Chimeric bPIV3/hPIV2 Virus Containing Human PIV2 F and HN Genes The F and HN genes of hPIV2 (Greer strain) were isolated by RT-PCR from hPIV2-infected LLC-MK2 cells. The 3.5 kb PCR fragment was sequenced to confirm the presence of the open reading frames. The bPIV3 F/HN intergenic region harboring the bPIV3 gene stop/gene start regions was introduced between the hPIV2 F and HN genes by overlapping PCR. This plasmid was further modified using overlapping PCR methods to construct chimeric F and HN genes such that the ectodomains of the F and HN proteins were derived from hPIV2 and the transmembrane and cytoplasmic regions originated from bPIV3. The plasmid containing the chimeric hPIV2/bPIV3 F and HN genes was sequenced and adjusted to the rule of six. The chimeric F and HN genes were isolated by digestion with Avr2 and Sal1. The resulting 3.2 kb fragment was then introduced into the bPIV3/L cDNA treated with Nhe1 and Sal1. The M/F and HN/L gene junctions of the full-length bPIV3/hPIV2 cDNA were sequenced to confirm the correct insertion of the F and HN genes.

The chimeric bPIV3/hPIV2 virus was recovered by reverse genetics in HeLa cells at 33 degrees C. The resulting virus was biologically cloned twice by limiting dilutions in Vero cells. High titer virus stocks were grown in Vero cells. The virus is characterized further in vitro and in vivo.

11. EXAMPLE 6

Determination of Amino Acid Substitution in bPIV3 L Gene which Confers Temperature-Sensitive and Attenuation Phenotypes This example describes a single amino acid mutation which, when introduced into the polymerase (L) gene of the bPIV3 genome and rescued as infectious virus, results in the recovered recombinant bPIV3 virus exhibiting temperature-sensitivity and decreased replication in the lungs of hamsters.

Studies were initiated to define the genetic basis of the temperature-sensitive and attenuation phenotypes of a recombinant bPIV3 (r-bPIV3) developed as a virus vaccine vector. Genetic data showed that the RNA genome of the mutant r-bPIV3 harbored four point mutations. Only one of them altered a single amino acid in a viral protein, the bPIV3 polymerase. To determine whether this single amino acid substitution in the polymerase specified either the temperature-sensitive or attenuation phenotype of r-bPIV3, a new virus, r-bPIV3/L, was recovered that contained the wild type amino acid in the polymerase protein. This new recombinant bPIV3/L lacked temperature-sensitivity in tissue culture. Replication of r-bPIV3/L was not restricted in either the lower or upper respiratory tract of Syrian golden hamsters. In summary, the single amino acid substitution in the bPIV3 polymerase was responsible for the temperature-sensitive and attenuation phenotypes observed for r-bPIV3. These results indicate that the polymerase gene of bPIV3 constitutes a major attenuation component of this virus vaccine vector. The attenuating effect of this single amino acid alteration in the bPIV3 polymerase protein may be used advantageously in the vaccine vector to modulate the expression levels of the inserted gene and for other purposes such as development of attenuated vaccines and vectors.

Bovine parainfluenza virus type 3 (bPIV3), a member of the paramyxoviridae family, is an enveloped, negative-sense, single strand RNA virus. The bPIV3 genome (Kansas 15626/84) is an uncapped RNA of 15,456 nucleotides in length (Haller et al., 2000). The 3' half of the viral genome encodes the nucleoprotein (NP) that encapsidates the viral RNA and the phosphoprotein (P), a polymerase-associated protein. The P protein plays a role in viral transcription and replication. In addition, the P open reading frame encodes three small proteins, C, D and V, by alternative molecular mechanisms. The L polymerase of bPIV3 is a large polypeptide, 2233 amino acids in length, and is thought to be a multifunctional protein that consists of multiple domains, including those required for association with the P protein, RNA binding, RNA polyadenylation, RNA transcription, and RNA replication.

bPIV3 (Kansas/15626/84) was isolated as a pathogen of cattle and has gained increased importance in recent years as a vaccine candidate for hPIV3, an infectious agent causing acute respiratory disease in infants. Vaccinees immunized with bPIV3 were protected from hPIV3 because bovine and human PIV3 are 25% related antigenically as was shown by cross-neutralization studies. Phase 2 clinical studies conducted showed that infants as young as 2 months old immunized with bPIV3 incurred protective immunity to hPIV3. Thus, it appears that bPIV3 can replicate in humans to levels that are sufficient for eliciting immune responses. During evolution bovine bPIV3 may have acquired genetic changes such that it displays a natural host pathogenic restriction in humans. Three genes encoding the NP, F and HN proteins may contribute to the restricted replication of bPIV3 in primates. The determinants present in each gene alone are insufficient to result in the attenuation phenotype observed for bPIV3. Due to the promising results obtained from the Phase 2 clinical trials evaluating bPIV3 as a hPIV3 vaccine candidate, bPIV3 was further developed as a virus vaccine vector to deliver foreign viral antigens (see, Examples 1 through 5).

The genetic determinants responsible for the temperature-sensitive and attenuation phenotypes of r-bPIV3, a novel virus vaccine vector were defined. An infectious cDNA of bPIV3 was constructed and infectious recombinant virus was rescued by reverse genetics. The linear gene organization of the r-bPIV3 genome is a 15,456 nucleotides long RNA genome. Upon sequencing of the bPIV3 cDNA, four sequence changes were identified that differed from the sequence of the biologically derived bPIV3. Two of these point mutations (nucleotides 6460 and 6463) were genetically engineered to generate a genomic marker in the viral RNA, an XhoI restriction enzyme site in the F gene. Neither of these nucleotide changes resulted in an amino acid substitution in the F protein. The third nucleotide change was located in the noncoding region of the L gene at position nucleotide 15354. This nucleotide change was not expected to yield an altered virus phenotype as it did not change the conserved gene stop sequences of the L gene or conserved trailer regions of the bPIV3 genome. The fourth single nucleotide alteration was identified in the L gene of r-bPIV3 at position 11946 encoding the viral polymerase. This nucleotide change caused a single amino acid substitution, an isoleucine to a valine, in the L protein of r-bPIV3. The contribution of this polymerase mutation to the temperature-sensitive and attenuation phenotypes of a previously described vectored vaccine virus, bovine/human PIV3, was studied in tissue culture and in hamsters.

Materials and Methods

Viruses and Cells

The bPIV3 (Kansas/15626/84), r-bPIV3, r-bPIV3/L, and bovine/human PIV3/L were grown in Vero cells in Opti-MEM medium (Gibco/BRL) containing antibiotics. The modified vaccinia virus Ankara (MVA-T7) which expresses the phage T7 RNA polymerase was grown in chicken embryonic kidney cells (SPAFAS). Vero and HeLa cells were maintained in MEM media (JRH Biosciences) supplemented with 10% fetal bovine serum (FBS), 2 mM L-glutamine, non-essential aminoacids, and antibiotics.

Construction of the pbPIV3/CAT Mini-Replicon

The pbPIV3/CAT mini-replicon was constructed to contain the antisense CAT gene flanked by the negative-sense bPIV3 leader linked to the hepatitis delta ribozyme (RZ) and T7 polymerase termination (T7T) signals, and the bPIV3 trailer sequences preceded by the T7 RNA polymerase promoter. The DNA fragment containing the T7T, the RZ and the bPIV3 leader region of pbPIV3/CAT was produced by two overlapping PCR fragments using two pair of primers encoding a KpnI restriction enzyme site and an XbaI site, respectively. The T7T/RBZ fragment was amplified from pRSV/CAT, the RSV minigenome plasmid, and the bPIV3 leader region was PCR amplified from the bPIV3 cDNA. These two PCR fragments contained overlapping sequences and were ligated into one fragment by annealing/extension through limited cycles of PCR. The PCR product was cleaved with KpnI and XbaI and introduced into the pRSV/CAT plasmid cut with KpnI and XbaI, thereby replacing the T7T/RZ/RSV leader in pRSV/CAT. The DNA fragment encoding the T7 RNA polymerase promoter and the bPIV3 trailer region was amplified using two oligos complementary to the bPIV3 trailer region encoding a PstI restriction enzyme site or the T7 RNA polymerase promoter encoding a HindIII restriction enzyme site. The PCR product was digested with Pst1 and HindIII and used to replace the complementary fragment in the pRSV/CAT plasmid to yield the pbPIV3/CAT mini-replicon plasmid.

Construction of the Full-Length r-bPIV3/L and Bovine/Human PIV3/L cDNAs

Employing the QuikChange mutagenesis kit (Stratagene) the single G residue at nucleotide position 11946 in the r-bPIV3 L gene was changed to an A residue in the plasmid L/pCITE described previously. The nucleotide change was confirmed by DNA sequencing. The altered L/pCITE plasmid was then digested with restriction enzymes SacI and PacI to liberate a 2.5 kb DNA fragment harboring the single nucleotide change. This DNA fragment was then introduced into two previously described plasmids, bPIV3/N/S and the plasmid containing the full-length bovine/human PIV3 cDNA, cleaved with SacI and PacI. The introduced sequence of the L gene of the full-length plasmids r-bPIV3/L and bovine/human PIV3/L were sequenced to verify the presence of the single nucleotide change.

Transfection of Infectious Full-Length Virus Antigenome-Containing Plasmids r-bPIV3/L and Bovine/Human PIV3/L HeLa cells (80% confluent) were infected with MVA-T7 at an MOI of 4. One hour post-infection, the full-length anti-genomic r-bPIV3/L plasmid (4 μg) or the bovine/human PIV3/L cDNA harboring plasmid were transfected into the MVA-T7-infected HeLa cells together with the NP/pCITE (0.4 μg), P/pCITE (0.4 μg), and L/pCITE (0.2 μg) expression plasmids in the presence of 9 μl LipofecTACE (Gibco/BRL) in 200 μl Opti-MEM (Gibco/BRL). Forty-eight hours post-transfection, the passage 0 (P0) cells and media were harvested together and subjected to one freeze-thaw cycle. The resulting P0 cell lysate was then used to infect fresh Vero cell monolayers in the presence of 40 μg/μl 1-beta-D-arabino-furanosylcytosine (ara C), a replication inhibitor of vaccinia virus, to generate a P1 virus stock. The media and cells from this infection cycle were harvested, freeze-thawed once and the presence of bPIV3 infection was confirmed by immunostaining of virus plaques using PIV3-specific antiserum (VMRD).

Recombinant Virus Stock Preparation

The P1 (passage 1) r-PIV3/L or bovine/human PIV3/L virus stocks were harvested from cells infected with P0 (passage 0). P0 virus stock was obtained from transfected cells. Following two cycles of plaque purification in Vero cells, high titer P2 (passage 2) virus stock was prepared in Vero cells and stored at −80° C.

Genotyping of r-bPIV3/L and Bovine/Human PIV3/L

Viral RNA of r-bPIV3/L or bovine/human PIV3/L was isolated from infected Vero cells using RNA STAT-50™ LS Reagent (Tel-Test, Inc.). To verify the genotypes of r-bPIV3/L or bovine/human PIV3/L, viral cDNA of r-bPIV3/L starting at nt 4500 was prepared using Superscript Reverse Transcriptase (Gibco/BRL). DNA fragments encompassing the region from nt 11000 to nt 13000 were amplified by PCR resulting in a 1.7 kb PCR product. The PCR products were sequenced to confirm the presence of the single nucleotide change in the viralpolymerase gene. The presence of the hPIV3 F and HN genes of bovine/human PIV3/L was also verified by RT-PCR and subsequent sequencing of the PCR products as described previously bPIV3 Mini-Genome Assay Subconfluent HeLa cells were infected with modified vaccinia virus Ankara (MVA) at an MOI of 5 (Wyatt et al., 1995). The infected cells were co-transfected using LipofecTACE (Gibco BRL/Life Sciences) with three plasmids encoding the P, NP and L bPIV3 genes and one reporter plasmid encoding the anti-genomic sequence of the chloramphenicol acetyl transferase (CAT) gene flanked by the bPIV3 leader and trailer. These plasmids were described previously in detail. The plasmids were transfected using the following amounts of DNA: NP/pCITE (200 ng), P/pCITE (200 ng), L/pCITE (200 to 600 ng) and bPIV3/CAT (500 ng). The cells were incubated for 5 hours at 33° C. Following a change of media, the incubation of the transfected cells was continued at 33° C., 37° C. and 39° C. Twenty-four or forty hours post-transfection, the cells were lysed and analyzed for the amount of CAT protein produced by carrying out CAT ELISAs (kit by Roche Molecular).

Growth Curves

Vero cells were grown to 90% confluence and infected at an MOI of 0.01 with bPIV3, r-bPIV3, or r-bPIV3/L. The infected monolayers were incubated at 37° C., 39° C., and 40° C. At 0, 24, 48, 72, 96 and 120 hours post-infection, cells and media were harvested together and stored at −80° C. Virus titers for each time point harvest were determined by $TCID_{50}$ assay in Vero cells.

Efficiency of Plaque Formation Assay

Plaque assays were carried out on Vero cells with bPIV3, r-bPIV3, r-bPIV3/L, and bovine/human PIV3/L. The infected monolayers were incubated at 35° C., 37° C., 38° C., 39° C., 39.5° C. and 40° C. Four days post-infection, the infected monolayers were immunostained using bPIV3-specific antisera (VMRD). The plaques were quantified and titers were determined at the different temperatures to identify the shut-off temperatures of the viruses.

Small Animal Studies

Five weeks old Syrian Golden hamsters (four animals per group) were infected with $5 \times 10^5$ pfu of bPIV3, r-bPIV3, r-bPIV3/L or bovine/human PIV3/L in a 100 μl volume. The three different groups were maintained separately in micro-isolator cages. Four days post-infection, the nasal turbinates and lungs of the animals were harvested, homogenized and stored at −80° C. The titers of virus present in the tissues was determined by $TCID_{50}$ assays in Vero cells.

Results

RNA Synthesis by Wild Type and Mutant bPIV3 Polymerases in a CAT Reporter Minigenome Assay at Different Temperatures Initially, we wanted to demonstrate that the single amino acid substitution present in the polymerase of r-bPIV3 would show an effect on global viral RNA synthesis in a chloramphenicol acetyl transferase (CAT) reporter minigenome assay. The single point mutation in the coding region of the r-bPIV3 L gene at nucleotide 11946 was reversed to the wild type sequence in the expression plasmid harboring the L gene (L/pCITE). DNA sequencing of the corrected L gene confirmed that no new mutations were introduced in the cloning process. MVA-T7-infected HeLa cells were transfected with plasmids encoding the wt bPIV3 P, NP, and wt or mutant L proteins along with the bPIV3/CAT minigenome plasmid, and the cells were incubated at 33, 37, or 39° C. The T7 RNA polymerase transcribes the minus sense CAT RNA, containing the 3' and 5' termini of bPIV3 genomic RNA. The NP protein will bind to the CAT transcripts such that they can serve as templates for replication and transcription by the viral polymerase complex. CAT protein present in the cell lysates was assayed by CAT ELISA. The minigenome assay could be used to test the viral transcription/replication activity of the template as well as functionality of the helper plasmids encoding the NP, P and L proteins of bPIV3, the proteins necessary for polymerase activity.

To determine the optimal wt L gene concentration resulting in a high CAT protein yield, increasing amounts of plasmid containing the wt L gene were tested in the minigenome assay system. The addition of 200 ng of wild type L resulted in high levels of minigenome transcription and replication as measured by CAT protein produced. CAT protein was not observed with bPIV3/CAT alone or in transfections each missing the L, NP or P plasmids. Transfection of HeLa cells with the mutant L gene plasmid showed a decreased production of CAT protein at 33° C. compared to lysates derived from transfections with the wild type L gene. Transfection with the mutant bPIV3 L gene resulted in approximately 30% activity of that observed when using the wt bPIV3 L gene at 33, 37 and 39° C. The CAT protein production by the mutant bPIV3 polymerase did not increase further with increasing temperature. These results suggested that the temperature-sensitive defect observed in r-bPIV3 may not be due to interaction of the L protein with NP or P but rather with other viral or cellular components involved in the viral life cycle.

Construction of the Full-Length Recombinant bPIV3 Harboring the Wild Type L Gene The L gene harboring the wild type coding sequence was introduced into the full-length bPIV3 cDNA and r-bPIV3/L virus was recovered by reverse genetics. The presence of the wt L gene coding sequence in the r-bPIV3/L genome was confirmed by sequencing RT-PCR fragments obtained from isolated r-bPIV3/L RNA. r-bPIV3/L was plaque purified twice in Vero cells and high titer virus stocks of $10^7$ pfu/ml were generated in Vero cells. Interestingly, the morphology of immuno-stained plaques of biologically derived bPIV3, r-bPIV3 and r-bPIV3/L showed that the plaques of r-bPIV3/L were similar in size to r-bPIV3 and still smaller than those from the biologically derived bPIV3. The determinants specifying burst size of bPIV3 may thus be located in genome stretches encompassing the nucleotide changes still present in r-bPIV3/L.

Temperature-Sensitivity of r-bPIV3/L Replication in Tissue Culture

To demonstrate that r-bPIV3/L harboring the wt L gene and the three nucleotide changes described above, still displayed a temperature-sensitive phenotype, its ability to form plaques at permissive and restrictive temperatures was tested. Plaque assays of bPIV3, r-bPIV3 and r-bPIV3/L were incubated at 37, 38, 39, 39.5, and 40° C. and after four days of incubation, plaques were visualized by immunoperoxidase staining with bPIV3 goat polyclonal antiserum. The results showed that r-bPIV3 was temperature-sensitive as was observed previously. The titer of r-bPIV3 decreased by approximately 1 $\log_{10}$ at 39° C. and was reduced by >3 $\log_{10}$ at 40° C. compared to the biologically derived bPIV3. The biologically derived bPIV3 did not change significantly in titer with increasing temperature. Interestingly, r-bPIV3/L displayed wild type virus behavior, a drop in titer with increasing temperature did not occur. This data indicated that the reversion of the amino acid in the L protein of r-bPIV3/L to wild type context obliterated the temperature-sensitive phenotype observed for r-bPIV3.

The multicycle replication of bPIV3, r-bPIV3 and r-bPIV3/L was studied in Vero cells. Briefly, subconfluent Vero cells were infected at an MOI of 0.01 and incubated at 37° C., 39° C. and 40° C. Time points were taken by harvesting the cells as well as the media at 0, 24, 48, 72, and 96 hours post-infection. The amount of virus at each time point was then determined by $TCID_{50}$ assay.

At 37° C., r-bPIV3/L replicated to levels observed for the biologically derived bPIV3 or r-bPIV3. All three viruses reached peak titers of 8 $\log_{10}$ $TCID_{50}$/ml by 48 hours post-infection. The titers of all three viruses were stable up to 96 hours post-infection at 37° C. r-bPIV3/L and bPIV3 yielded similar titers at 39° C. Their peak titers were 8.1 and 8.6 $\log_{10}$ $TCID_{50}$/ml at 48 hours post-infection, respectively. At 39° C., r-bPIV3 displayed a delayed onset of replication and a reduced peak titer of 7.0 $\log_{10}$ $TCID_{50}$/ml compared to bPIV3. r-bPIV3 displayed a temperature-sensitive phenotype in Vero cells at 39° C. as was previously observed. The temperature-sensitive phenotype of r-bPIV3 was more obvious at 40° C. r-bPIV3 displayed dramatic 7 and 5 $\log_{10}$ reductions in virus titers at 40° C. compared to its peak titers at 37° C. and 39° C., respectively The biologically derived bPIV3 was also reduced by 2.3 $\log_{10}$ at 40° C. compared to its peak titer at 37° C. This decrease in titers of bPIV3 at 40° C. was observed previously despite the viability of Vero cells at 40° C. Interestingly, r-bPIV3/L replicated as efficiently as the biologically derived bPIV3 at 40° C., reaching peak titers at 72 hours post-infection. This data further substantiated that the amino acid change in the L protein of r-bPIV3/L to the wild type context resulted in a recombinant virus lacking a temperature-sensitive phenotype.

Determination of the Attenuation Phenotype of r-bPIV3/L in Hamsters

In order to demonstrate that the amino acid change in the polymerase protein to wild type context in r-bPIV3/L had an effect on the attenuation phenotype of r-bPIV3, we tested the replication of bPIV3, r-bPIV3 and r-bPIV3/L in vivo in Syrian golden hamsters. Briefly, hamsters were inoculated intranasally with $5 \times 10^5$ pfu of bPIV3, r-bPIV3 or r-bPIV3/L and four days post-infection the animals were sacrificed. The lungs and nasal turbinates were harvested and virus titers were determined by $TCID_{50}$ assays using Vero cells. r-bPIV3/L. replicated to 5.3 $\log_{10}$ $TCID_{50}$/g tissue in the nasal turbinates and lungs of hamsters which were the same levels of replication observed for the biologically derived bPIV3. r-bPIV3 replicated to 5.0 $\log_{10}$ $TCID_{50}$/g tissue in the nasal turbinates but showed by 1.8 $\log_{10}$ decreased titers in the lungs compared to bPIV3 as was observed previously. These results showed that the single amino acid substitution in the r-bPIV3 polymerase specified not only the temperature-sensitive phenotype but also the attenuation phenotype of r-bPIV3.

Analysis of the Location of the Mutation in the Polymerase Gene

Sequence alignments of the polymerase genes of a number of parainfluenza viruses were performed to determine the degree of conservation of the altered amino acid residue at position 1103 in the L protein and the region surrounding it, among the various viruses. Interestingly, the isoleucine to valine amino acid substitution occurred in a 20 amino acid stretch of the polymerase gene that was highly conserved among bPIV3, hPIV3, hPIV1 and Sendai virus. The biologically derived bPIV3 and hPIV3 displayed an isoleucine at amino acid position 1103, r-bPIV3 had a valine, and hPIV1 and Sendai virus showed a leucine residue in this position. Less closely related viruses such as human parainfluenza virus type 2, mumps, or measles viruses displayed a valine or leucine, respectively, in this position. In contrast, the polymerase protein of hRSV did not show homology at the amino acid level for this region of the polymerase protein with those of the parainfluenza viruses.

The region of the r-bPIV3 L protein harboring the substituted amino acid was further compared to the location of the mutations present in cp45 hPIV3 responsible for its temperature-sensitive and attenuation phenotype. Three amino acid substitutions, Y942H, L992F, T1558I, in the L protein of hPIV3 resulted in temperature-sensitive phenotypes alone or in combination. In the linear context of the polymerase protein, the V1103I change of r-bPIV3 was not in close proximity to the alterations observed for cp45 hPIV3. The closest amino acid substitution of cp45 hPIV3 was L992F, although it was still greater than 100 amino acids upstream of the I1103V change observed in r-bPIV3. However, in the native conformation of the polymerase protein, all four of these amino acid substitutions may be in close proximity to each other.

Effect of the Polymerase Mutation on a Vectored Vaccine Virus, Bovine/Human PIV3

One application of bPIV3 as a vaccine virus vector is the introduction of the surface glycoproteins of the three serotypes of human parainfluenza virus, hPIV1, 2, and 3 to generate vaccines for hPIV1, 2, and 3. We have previously described the phenotypes of bovine/human PIV3, a putative vaccine for hPIV3 that contained the hPIV3 F and HN genes replacing those of bPIV3. Bovine/human PIV3 displayed a shut-off temperature of 39.5° C. and was restricted by 1.5 $\log_{10}$ $TCID_{50}$/g tissue for replication in the lungs of hamsters. We could not differentiate whether the cause for the observed phenotypes of bovine/human PIV3 was due to the polymerase mutation or the introduction of foreign glycoprotein genes. The polymerase mutation was therefore corrected to wild type context in the full-length cDNA of bovine/human PIV3. Recombinant virus, bovine/human PIV3/L, was rescued by reverse genetics and characterized for temperature-sensitivity and replication in hamsters. An efficiency of plaque formation experiment was carried out using Vero cells to determine whether bovine/human PIV3/L was temperature-sensitive. The results showed that bovine/human PIV3/L did not display significantly decreased virus titers at temperatures as high as 40° C. Bovine/human PIV3/L was also evaluated for replication in the lower and upper respiratory tracts in Syrian golden hamsters.

Discussion

This example shows that a single nucleotide alteration in the polymerase gene of bPIV3 results in a recombinant virus that displayed a temperature-sensitive phenotype as well as restricted replication in the lower respiratory tract of hamsters. The amino acid change in the L gene thought most likely to be responsible for these phenotypes was reversed to wild type context by site-directed mutagenesis and the resulting wild type gene was assayed for activity and function in the bPIV3 minigenome assay. The results obtained from this assay showed that indeed the mutant L gene displayed a three to-four-fold lower viral RNA synthesis activity compared to the wild type L gene. The observation that the amount of activity of the mutant L gene did not decrease further with increasing temperature suggested that the interactions with NP and P were not responsible for the temperature-sensitive phenotype of r-bPIV3 but rather interactions of the L protein with other cellular or viral factors.

Upon introducing the corrected L gene into the full-length bPIV3 cDNA, a recombinant virus, r-bPIV3/L that harbored the wild type L gene coding region, was recovered.

r-bPIV3/L differed from r-bPIV3 only by the single amino acid that was reversed to wild type context. Thus, r-bPIV3/L still maintained the other three nucleotide alterations present in the F gene and the untranslated region of the L gene of r-bPIV3. Characterization of the in vitro replication phenotype of r-bPIV3/L showed that r-bPIV3/L was not temperature-sensitive for growth in tissue culture. r-bPIV3/L yielded the same titers as the biologically derived bPIV3 at 37, 38, 39, 39.5 and 40° C. In multi-cycle growth curves, r-bPIV3/L and bPIV3 displayed similar kinetics of virus replication. Both viruses reached peak titers at the same time points and the onset of replication was comparable at all temperatures. r-bPIV3/L did not display a temperature-sensitive phenotype for growth in tissue culture. The ability of r-bPIV3/L to replicate in the upper and lower respiratory tracts of Syrian golden hamsters was also tested since r-bPIV3 displayed a by 2 $\log_{10}$ decreased replication in the lungs of hamsters. Again, r-bPIV3/L behaved similar to the biologically derived bPIV3 and unlike r-bPIV3. r-bPIV3/L replicated in both the lower and upper respiratory tracts of hamsters to wild type levels. Thus, r-bPIV3/L did not display an attenuation phenotype for replication in hamsters. In summary, r-bPIV3/L harboring a virus genome in which only a single amino acid was altered to reflect the wild type L gene sequence, resembled the biologically derived bPIV3 more closely than the previously isolated and characterized r-bPV3 that was shown to be temperature-sensitive for growth at 39° C.

Alignment of the L proteins of bPIV3, hPIV3, hPIV1 and Sendai virus showed that amino acid 1103 is located in a highly conserved stretch of the polymerase gene. Although amino acid 1103 was not located in one of the four conserved polymerase motives A, B, C or D. Bovine and human PIV3 display an isoleucine at this position, while hPIV1 and Sendai viruses have a leucine. The conservative substitution of the isoleucine at 1103 with a valine in the bPIV3 polymerase resulted in a surprisingly dramatic effect in r-bPIV3. Isoleucine and valine harbor similar side chains differing only by a single methyl group. However, there appears to exist an absolute requirement for an isoleucine or a leucine in this position for parainfluenza viruses. In contrast, related paramyxoviruses such as bPIV2, mumps, and measles can tolerate a valine or leucine in this position of the polymerase protein. Similar dramatic effects on virus replication upon amino acid substitutions have been observed previously. A conservative amino acid substitution in the polymerase of hPIV1 had an effect on both viral transcription and replication. Here a leucine to isoleucine substitution in the hPIV1 polymerase at position 1558 showed a dramatic effect on virus replication. This amino acid substitution did not effect viral transcription by the hPIV1 polymerase at the permissive temperature, but reduced transcription by 50% at 39.6° C. In vitro replication activity of the hPIV1 polymerase was reduced by 85% at the permissive temperature. In contrast, the replication activity in vivo was better than wild type L at the permissive temperature, but decreased rapidly at 37° C. and was inactive at 39.6° C. These results showed that it is very difficult to predict the phenotype of a virus based on rationally designed and introduced mutations in the viral polymerase protein. It is also difficult to establish a correlation between the severity of the virus defect and the degree of severity of ammo acid substitution.

The invention provides for temperature sensitive attenuated bPIV3 viruses wherein the viruses contain a recombinant genome wherein the polymerase (L) gene specifies a residue other than leucine or isoleucine at position 1103; and generally encodes a naturally occurring amino acid residue at position 1103 which is selected from the group consisting of: glycine, alanine, valine, phenylalanine, tyrosine, tryptophan, methionine, cysteine, serine, threonine, arginine, lysine, histidine, proline, glutamate, aspartate, glutamine, and asparagine. In a preferred embodiment, amino acid 1103 is valine.

The polymerase mutation studied here further specified the temperature-sensitive and attenuation phenotypes of bovine/human PIV3, a vectored vaccine virus described previously (supra and Haller et al., 2000). The surface glycoprotein genes F and HN of bPIV3 and hPIV3 are closely related and display 77 and 80% amino acid identities at the amino acid level, respectively. The close relationship of the surface glycoprotein proteins of bovine and human PIV3 was expected to minimize the impact of introducing foreign genes into bPIV3. Thus, the polymerase mutation present in bovine/human PIV3 was the cause of the resulting phenotypes of this virus. The implications of this polymerase mutation for the use of bPIV3 as a virus vaccine vector are the availability of a molecular tool to define the expression levels of the introduced genes. In cases where low levels of the protein of interest are required, the r-bPIV3 vector will be employed. However, when higher levels of foreign protein are desired, r-bPIV3/L will be used. In summary, in this example we have identified a polymerase mutation of bPIV3 that will allow fine tuning of the degree of expression of the gene of interest in bPIV3 vactor backbones. This will be advantageous for a virus vaccine vector and other uses.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A pharmaceutical composition comprising:
   (a) a recombinant parainfluenza virus (PIV) comprising:
      (i) nucleotide sequences of a Kansas-strain bovine PIV type 3 genome; and
      (ii) one or more heterologous sequence,
         wherein said one or more heterologous sequence has been added to said Kansas-strain bovine PIV genome or has been substituted for nucleotide sequences of said Kansas-strain bovine PIV genome at nucleotide position 5041, nucleotide position 8529, or the hemagglutinin-neuraminidase glycoprotein gene; and
   (b) a pharmaceutically acceptable excipient.

2. The pharmaceutical composition of claim 1 wherein the heterologous sequence is derived from respiratory syncytial virus (RSV), PIV, New Castle Disease virus, Sendai virus, Infectious Laryngotracheitis virus, or influenza virus.

3. A pharmaceutical composition comprising:
   (a) a recombinant parainfluenza virus (PIV) comprising:
      (i) nucleotide sequences of Kansas-strain bovine PIV type 3 genome, wherein the nucleotide sequences comprise nucleotides 1-5041 and nucleotides 8529-15,456 of the Kansas strain bovine PIV type 3 genome; and
    (ii) F and HN gene sequences of human PIV type 3; and
  (b) a pharmaceutically acceptable excipient.
4. A pharmaceutical composition comprising:
  (a) a recombinant parainfluenza virus (PIV) comprising:
    (i) nucleotide sequences of Kansas-strain bovine PIV type 3 genome; and
    (ii) the F and HN gene sequences of human PIV type 3,
      wherein PCR amplification of nucleotide 5,255 to 6,255 of the recombinant PIV results in a DNA fragment that is recognized by restriction endonucleases Sac I and Bgl II; and PCR amplification of nucleotide 9,075 to 10,469 of the recombinant PIV results in a DNA fragment that is recognized by restriction endonucleases Pvu II and Bam HI; and
  (b) a pharmaceutically acceptable excipient.
5. A pharmaceutical composition comprising:
  (a) a recombinant parainfluenza virus (PIV) comprising:
    (i) nucleotide sequences of Kansas-strain bovine PIV type 3 genome,
      wherein the nucleotide sequences comprise nucleotides 1-5041 and nucleotides 8529-15,456 of the Kansas strain bovine PIV type 3 genome; and
    (ii) one or more sequences derived from RSV, PIV, New Castle Disease virus, Sendai virus, Infectious Laryngotracheitis virus or influenza virus; and
  (b) a pharmaceutically acceptable excipient.
6. A pharmaceutical composition comprising:
  (a) a recombinant parainfluenza virus (PIV) comprising:
    (i) nucleotide sequences of Kansas-strain bovine PIV type 3 genome,
      wherein the nucleotide sequences comprise nucleotides 1-5041 of the Kansas-strain bovine PIV type 3 genome; and
    (ii) one or more sequences derived from RSV, PIV, New Castle Disease virus, Sendai virus, Infectious Laryngotracheitis virus or influenza virus; and
  (b) a pharmaceutically acceptable excipient.
7. A pharmaceutical composition comprising:
  (a) a recombinant parainfluenza virus (PIV) comprising:
    (i) nucleotide sequences of Kansas-strain bovine PIV type 3 genome,
      wherein the nucleotide sequences comprise nucleotides 8,529-15,456 of the Kansas-strain bovine PIV type 3 genome; and
    (ii) one or more sequences derived from RSV, PIV, New Castle Disease virus, Sendai virus, Infectious Laryngotracheitis virus or influenza; and
  (b) a pharmaceutically acceptable excipient.

8. The pharmaceutical composition of claim 2 wherein the heterologous sequence is derived from RSV or PIV.

9. The pharmaceutical composition of claim 2 wherein the heterologous sequence is derived from human RSV or human PIV.

10. The pharmaceutical composition of claim 5, 6, or 7 wherein the one or more sequences are derived from RSV, PIV, or influenza virus.

11. The pharmaceutical composition of claim 5, 6, or 7 wherein the one or more sequences are derived from human RSV, human PIV, or human influenza virus.

12. The pharmaceutical composition of claim 5, 6, or 7 wherein the one or more sequences are human PIV 3 F and HN gene sequences.

13. The pharmaceutical composition of claim 5, 6, or 7 wherein the one or more sequences are human RSV glycoprotein gene sequences.

14. The pharmaceutical composition of claim 1, 3, 4, 5, 6, or 7 which is suitable for oral, intradermal, intramuscular, intraperitoneal, intravenous, subcutaneous, or intranasal administration.

15. The pharmaceutical composition of claim 1, 3, 4, 5, 6, or 7 further comprising an adjuvant.

16. The pharmaceutical composition of claim 15 wherein the adjuvant is a mineral gel, a surface active substance, a peptide, or an oil emulsion.

17. The pharmaceutical composition of claim 1, 3, 4, 5, 6, or 7 wherein the recombinant parainfluenza virus is attenuated.

18. The pharmaceutical composition of claim 1, 2, 3, 4, 5, 6, 7, 8, or 9 which comprises $5 \times 10^5$ plaque forming units of the recombinant parainfluenza virus.

19. A method comprising:
  administering the pharmaceutical composition of any one of claims 1, 2, 3, 4, 5, 6, 7, 8, or 9 to a subject.

20. A method comprising:
  administering the pharmaceutical composition of claim 11 to a subject.

21. A method comprising:
  administering the pharmaceutical composition of claim 18 to a subject.

* * * * *